United States Patent
Nakatsugawa et al.

(10) Patent No.: US 8,796,633 B2
(45) Date of Patent: Aug. 5, 2014

(54) RADIATION IMAGING DEVICE, SYSTEM, AND METHOD

(75) Inventors: Haruyasu Nakatsugawa, Kanagawa (JP); Naoyuki Nishino, Kanagawa (JP); Naoto Iwakiri, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 227 days.

(21) Appl. No.: 13/448,148

(22) Filed: Apr. 16, 2012

(65) Prior Publication Data

US 2012/0267535 A1    Oct. 25, 2012

(30) Foreign Application Priority Data

Apr. 25, 2011   (JP) ................. 2011-097089

(51) Int. Cl.
*G01T 1/20* (2006.01)
*H01L 27/146* (2006.01)

(52) U.S. Cl.
CPC ........ *G01T 1/2002* (2013.01); *H01L 27/14663* (2013.01)
USPC .................................................. 250/370.11

(58) Field of Classification Search
CPC ................. H01L 27/14663; G01T 1/2002
USPC ................................... 250/370.11
See application file for complete search history.

(56) References Cited

U.S. PATENT DOCUMENTS

| | | | |
|---|---|---|---|
| 5,905,772 A | 5/1999 | Rutten et al. | |
| 5,973,327 A * | 10/1999 | Moy et al. | 250/370.09 |
| 7,231,018 B2 * | 6/2007 | Morii et al. | 378/97 |
| 2003/0160185 A1 * | 8/2003 | Homme | 250/483.1 |
| 2008/0099694 A1 | 5/2008 | Shoji et al. | |
| 2011/0073768 A1 * | 3/2011 | Ohta et al. | 250/370.08 |

FOREIGN PATENT DOCUMENTS

JP        2007-147370 A      6/2007

* cited by examiner

*Primary Examiner* — Constantine Hannaher
(74) *Attorney, Agent, or Firm* — Jean C. Edwards; Edwards Neils PLLC

(57) ABSTRACT

A radiation detector includes a sensor panel, a scintillator panel, a reflective layer, and a radiation irradiation detecting photodetector laminated in this order from a side of a radiation receiving surface. Radiation transmitted through a patient's body enters the scintillator panel through the sensor panel, and is converted into light. The converted light propagates through columnar crystals in the scintillator panel with total internal reflection. A part of the light reaches the sensor panel, while the remains reach the reflective layer. The light reaching the sensor panel is detected by photoelectric converters. Out of the light reaching the reflective layer, a short wavelength component with a relatively high refractive index is specularly reflected to the sensor panel. A long wavelength component with a relatively low refractive index is transmitted through the reflective layer, and enters the radiation irradiation detecting photodetector, which detects a start of radiation irradiation.

20 Claims, 17 Drawing Sheets

RADIATION IMAGING DEVICE, SYSTEM, AND METHOD

CROSS-REFERENCE TO RELATED APPLICATIONS

The present application claims priority from Japanese Patent Application No. 2011-097089, filed Apr. 25, 2011, the contents of which are herein incorporated by reference in their entirety.

BACKGROUND OF THE INVENTION

1. Field of the Invention

The present invention relates to a radiation imaging device having a scintillator for converting radiation into light, and a radiation imaging system and method using the radiation imaging device.

2. Description Related to the Prior Art

A radiation imaging device (generally called electronic cassette) that contains an indirect conversion type of radiation detector is in practical use for radiography. The indirect conversion type of radiation detector is provided with a scintillator and a sensor panel opposed to each other. The scintillator converts radiation e.g. X-rays into light. The sensor panel has a two-dimensional array of photoelectric converters, each for converting the light produced by the scintillator into an electric signal. There is also known a radiation detector having a reflective layer (refer to US Patent Application Publication No. 2008/0099694, for example). In this radiation detector, the sensor panel is disposed on one surface of the scintillator in a light exit direction, while the reflective layer is disposed on the other surface of the scintillator in a direction opposite to the light exit direction. The reflective layer reflects the light from the scintillator to the sensor panel, to make effective use of the light produced by the scintillator.

There is a type of scintillator that is composed of a plurality of columnar crystals erected along the light exit direction. The columnar crystals are manufactured by evaporation of cesium iodide (CsI) onto a substrate. This type of scintillator can reduce dispersion of the light produced in the scintillator, because the light propagates through the columnar crystals with total internal reflection, due to a light guide effect of the columnar crystals, heading for the sensor panel. Accordingly, the radiation imaging device using the scintillator with the columnar crystals can prevent deterioration of image sharpness, when producing an image by detecting the radiation.

In the scintillator having the columnar crystals, a gap is left between the adjacent columnar crystals to prevent the occurrence of crosstalk. The crosstalk is a phenomenon in which light propagating through one columnar crystal partly moves to another adjacent columnar crystal, when the two columnar crystals contact each other. The occurrence of the crosstalk causes a large deviation between a light emission point in the scintillator and a light incident point on the sensor panel, and results in a blur in a radiographic image.

The crosstalk occurs even if the columnar crystals are not in contact. As shown in FIG. 17, light 122 propagating through a columnar crystal 121a of a scintillator 120 with total internal reflection goes out of the columnar crystal 121a and enters an adjacent columnar crystal 121b, when an incident angle θx of the light 122 with respect to an interior wall of the columnar crystal 121a is less than a critical angle θx. When a refractive index of columnar crystals made of CsI is 1.8 and a refractive index of air present between the columnar crystals is 1.0, the critical angle θx is approximately 34°.

Moreover, the light 122 having entered the columnar crystal 121b from the columnar crystal 121a sometimes travels through further other columnar crystals, and reaches a columnar crystal far away from the columnar crystal 121a. This is because a gap between the columnar crystals is very small, and the light 122 having gone out of the columnar crystal 121a is hardly refracted. Especially, since a long wavelength component 122b of the light 122 is harder to refract than a short wavelength component 122a, an incident angle of the long wavelength component 122b on the columnar crystal 121b is maintained at a value less than the critical angle θx. Note that, the short wavelength component denotes light in a wavelength band of 620 nm or less in the case of a scintillator made of CsI:Tl, for example. The long wavelength component denotes light in a wavelength band over 620 nm.

The crosstalk caused by the incident angle, as described above, occurs not only in light propagating directly from the scintillator to the sensor panel, but also in light reflected from the reflective layer to the sensor panel. As shown in FIG. 18, most of the radiation incident upon the scintillator 120 is converted into the light at a radiation incident area, which is on a radiation incident side of the scintillator 120. The short wavelength component 122a of the light, having a relatively high refractive index, propagates through the columnar crystal 121a with the total internal reflection to the reflective layer 124. Even if the incident angle of the short wavelength component 122a with respect to the reflective layer 124 is less than the critical angle and the short wavelength component 122a enters the columnar crystal 121b from the columnar crystal 121a, the light incident point on the sensor panel 125 does not much deviate from the light emission point in the scintillator 120, because soon afterward the short wavelength component 122a has the incident angle equal to or more than the critical angle by refraction.

On the other hand, as shown in FIG. 19, since the long wavelength component 122b produced in the radiation incident area of a columnar crystal 121c of the scintillator 120 is harder to refract than the short wavelength component 122a, the long wavelength component 122b largely deviates from the light emission point before reaching the reflective layer 124. The long wavelength component 122b further deviates from the light emission point until being reflected from the reflective layer 124 and reaching the sensor panel 125, and is incident upon the sensor panel 125 at the light incident point far away from the light emission point. Note that, FIGS. 18 and 19 show just apart of the radiation detector, and the long wavelength component 122b does not necessarily propagate from one end of the sensor panel 125 to the other end thereof.

The indirect conversion type of radiation detector adopts either of an irradiation side sampling (ISS) method as shown in FIG. 18 and a penetration side sampling (PSS) method, which is not shown. In the ISS method, the sensor panel 125, the scintillator 120, and the reflective layer 124 are disposed in this order from the radiation incident side. The scintillator 120 converts the radiation that has been transmitted through the sensor panel 125 into light, and the sensor panel 125 detects the light. In the PSS method, a reflective layer, a scintillator, and a sensor panel are disposed in this order from the radiation incident side. The scintillator converts radiation that has been transmitted through the reflective layer into light. In the PSS method, the light produced in the radiation incident area of the scintillator is reflected from the reflective layer, which is disposed near the radiation incident area, to the sensor panel. On the other hand, in the ISS method, the light produced in the radiation incident area of the scintillator propagates to the reflective layer through the scintillator. The light is reflected from the reflective layer, and propagates through the scintillator to the sensor panel. Thus, a light propagation distance of the ISS method is twice as large as that of the PSS method, and the ISS method is more susceptible to the crosstalk.

The radiation detector disclosed in the U.S. Patent Application Publication No. 2008/0099694 has an absorbing layer provided between the scintillator and the reflective layer. The absorbing layer absorbs the long wavelength component of the light, for the purpose of preventing the blur of the radiographic image caused by the long wavelength component of the light produced by the scintillator. There is also known a radiation imaging device having the function of light reset (also called bias light emission, light calibration, or the like) in which reset light is applied from a light source to the photoelectric converters of the sensor panel. The application of the reset light improves deterioration in properties of the photoelectric converters due to an extended period of use, and stabilizes dark current occurring in the photoelectric converters (refer to Japanese Patent Laid-Open Publication No. 2007-147370). This function facilitates reducing deterioration in a motion radiographic image, for example. It is also known that infrared light is suitably used as the reset light (refer to U.S. Pat. No. 5,905,772, for example).

According to the radiation detector of the US Patent Application Publication No. 2008/0099694, provision of the absorbing layer to remove the long wavelength component causes high cost. Additionally, effective use of the long wavelength component of the light is desired, though the long wavelength component is unused at present.

In the above radiation detector of the ISS method, the reset light source cannot be situated on the sensor panel, because the sensor panel is disposed on the radiation incident side. To be more specific, if the light source is disposed on the sensor panel, the radiation is absorbed by the light source. Furthermore, if the light source is composed of an LED, an EL element, or the like, the light source sometimes emits the reset light involuntarily in response to application of the radiation. Since the radiation detector of the ISS method is provided with the reflective layer on the light exit side of the scintillator, the reset light source cannot be provided on the light exit side of the scintillator. In other words, if the reset light source is provided on the reflective layer, the reset light cannot be transmitted through the reflective layer and hence cannot be applied to the sensor panel.

SUMMARY OF THE INVENTION

A main object of the present invention is to prevent a blur of a radiographic image due to a long wavelength component of light produced by a scintillator without using an absorbing layer of the long wavelength component.

Another object of the present invention is to make effective use of the long wavelength component of the light, and provide both a reflective layer and a reset light source in a radiation detector.

A radiation imaging device according to the present invention includes a scintillator for converting applied radiation into light, a sensor panel disposed on a light exit side of the scintillator, and a reflective layer disposed on a side opposite to the light exit side of the scintillator. The sensor panel has a two-dimensional array of photoelectric converters each for converting the light into an electric signal. The reflective layer reflects a short wavelength component of the light to the sensor panel, while transmitting a long wavelength component of the light.

It is preferable that the light is reflected or transmitted selectively in accordance with a wavelength of the light. The reflective layer is preferably a dichroic filter.

The radiation imaging device may further include a protective film for covering an outer periphery of the scintillator. The protective film holds the reflective layer such that the reflective layer tightly contacts the scintillator.

The radiation imaging device may further include a radiation irradiation detecting photodetector for detecting the long wavelength component transmitted through the reflective layer, and a controller for resetting all the photoelectric converters of the sensor panel based on detection of the long wavelength component. The radiation irradiation detecting photodetector may be made of an organic photoelectric conversion material.

The radiation irradiation detecting photodetector may include a plurality of photodetecting sections arranged on the reflective layer. Each of the photodetecting sections has a detection area larger than one of the photoelectric converters of the sensor panel.

The radiation imaging device may further include a reset light source for applying reset light of a long wavelength to the photoelectric converters of the sensor panel through the reflective layer and the scintillator. The reset light source and the radiation irradiation detecting photodetector may be disposed in a tiled manner on the reflective layer on a side opposite to a side facing to the scintillator.

The radiation irradiation detecting photodetector and the reset light source may be glued on the reflective layer with a transparent adhesive.

The reset light source preferably has such a size as to cover all the photoelectric converters of the sensor panel, and is disposed in such a position as to be opposed to all the photoelectric converters of the sensor panel. The radiation irradiation detecting photodetector is preferably disposed around the reset light source.

The sensor panel is preferably disposed on a radiation incident side of the scintillator, and the radiation enters the scintillator through the sensor panel.

The long wavelength component of the light preferably has a wavelength longer than an emission peak wavelength of the scintillator.

The scintillator is preferably composed of a plurality of erected columnar crystals. The scintillator is preferably made of cesium iodide. A filling rate of the cesium iodide to the scintillator is preferably 70 to 85%. The photoelectric converter preferably has an organic photoelectric conversion film.

A radiation imaging system according to the present invention includes a radiation generator for generating radiation and the above radiation imaging device for imaging the radiation.

A radiation imaging method includes the steps of converting incident radiation into light by a scintillator; entering the light into a reflective layer to make a short wavelength component of the light reflected to a sensor panel, while making a long wavelength component of the light transmitted through the reflective layer; detecting the long wavelength component transmitted through the reflective layer; and resetting all photoelectric converters provided in the sensor panel in response to the detection of the long wavelength component.

According to the present invention, the short wavelength component of the light, which hardly causes optical crosstalk, is reflected from the reflective layer, in order to prevent reduction in a light amount detected by the sensor panel. The long wavelength component of the light, which tends to cause the optical crosstalk, is selectively transmitted through the reflective layer, to prevent the occurrence of the crosstalk. Furthermore, since the long wavelength component of the light transmitted through the reflective layer is used for detecting a start of radiation irradiation, the long wavelength component of the light is used effectively.

According to the present invention, since the reflective layer transmits light in a long wavelength, the reset light source can be disposed on the reflective layer.

BRIEF DESCRIPTION OF THE DRAWINGS

For more complete understanding of the present invention, and the advantage thereof, reference is now made to the following descriptions taken in conjunction with the accompanying drawings, in which.

DESCRIPTION OF THE PREFERRED EMBODIMENTS

First Embodiment

Figure 1:
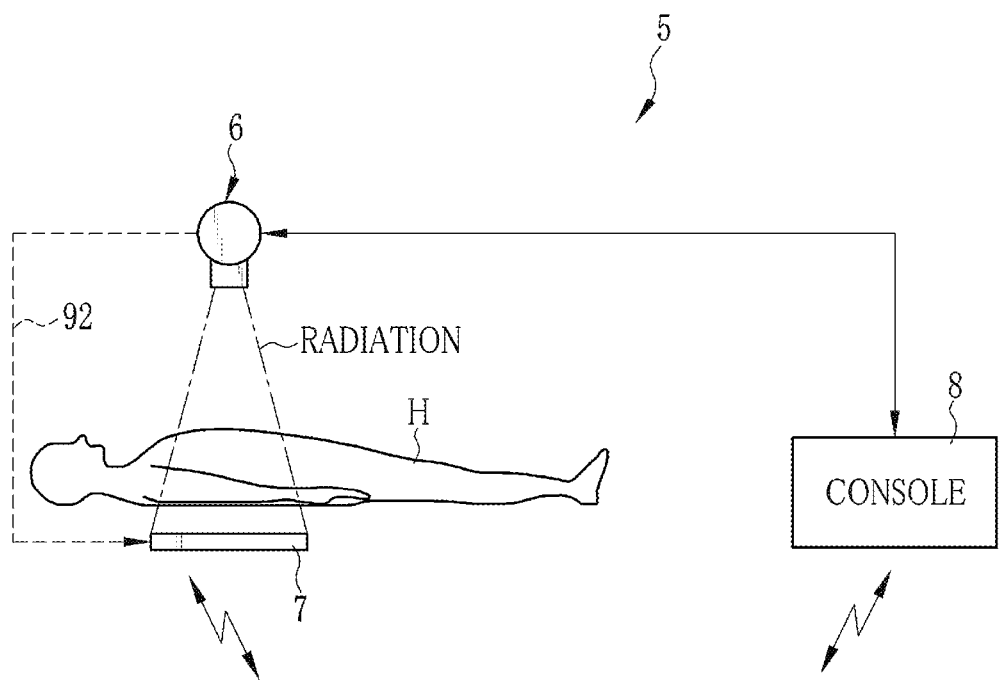
FIG. 1 is a schematic view of a radiation imaging system.

As shown in FIG. 1, a radiation imaging system 5 according to the present invention is constituted of a radiation generator 6, a radiation imaging device (electronic cassette) 7, and a console 8. The radiation generator 6 applies radiation, for example, X-rays to a patient H. The radiation imaging device 7 captures a radiographic image based on the radiation that has been transmitted through the patient H. The console 8 controls the radiation generator 6 and the radiation imaging device 7.

Figure 2:
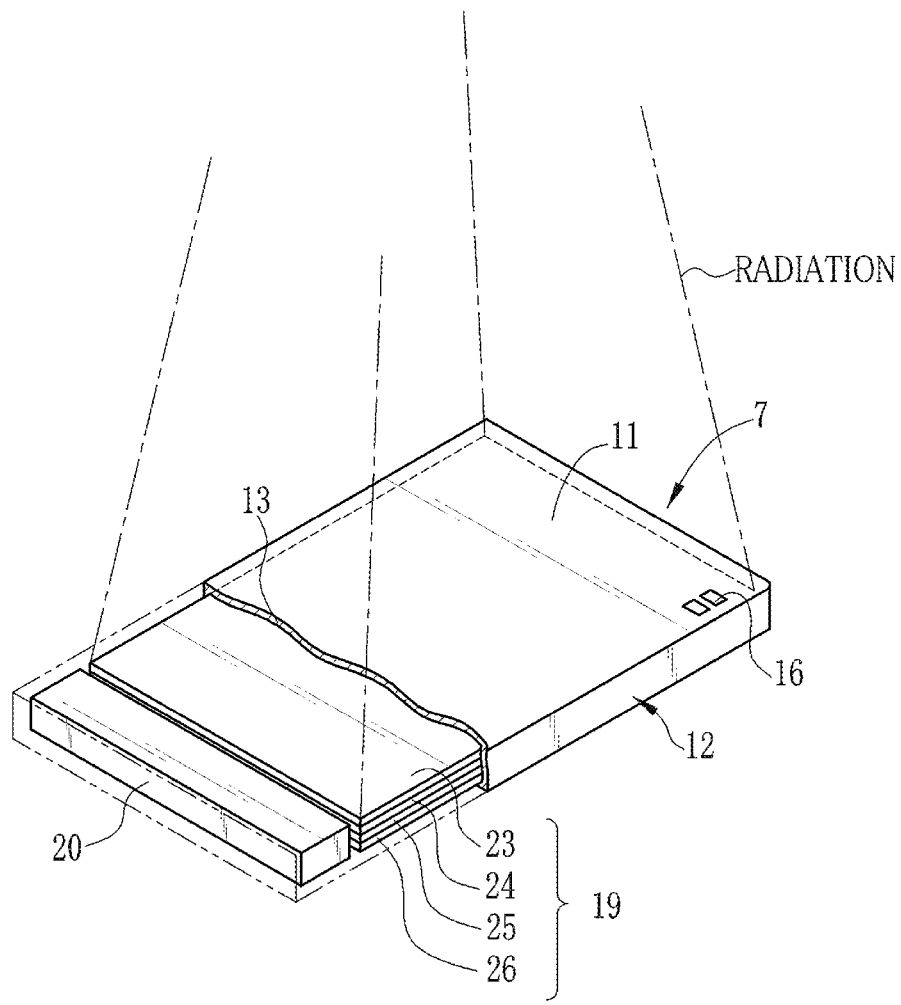
FIG. 2 is a perspective view of a partly broken radiation imaging device.

As shown in FIG. 2, the radiation imaging device 7 has an approximately box-shaped housing 12. The housing 12 is provided with a top plate 13 at its top surface, which functions as a radiation receiving surface 11. The top plate 13 is made of carbon or the like, which allows the radiation to transmit therethrough and ensures sufficient strength. The other portion of the housing 12 excepting the top plate 13 is made of a radiation transparent material, for example, ABS resin. Note that, the housing 12 has the same size as that of a conventional cassette for recording an image on a photosensitive material by the radiation, and is usable in a conventional radiation imaging system instead of the conventional cassette.

The radiation receiving surface 11 of the radiation imaging device 7 is provided with an indicator 16 having plural LEDs. The indicator 16 indicates an operation state of the radiation imaging device 7, such as an operation mode (for example, on standby, on data transmission, and the like) and remaining battery charge. Note that, the indicator 16 may be composed of another type of light emitting elements other than the LEDs, or a display monitor such as a liquid crystal display or an organic EL display. The indicator 16 may be provided in another location other than the radiation receiving surface 11.

The housing 12 of the radiation imaging device 7 contains a panel-shaped radiation detector 19 that detects the radiation transmitted through a body of the patient H. The radiation detector 19 is opposed to the radiation receiving surface 11 in the housing 12. The housing 12 also contains a case 20 along a short side of the housing 12 on one end of the radiation receiving surface 11. The case 20 encloses various electric circuits including a microcomputer and a chargeable and detachable battery (secondary battery). The battery contained in the case 20 supplies electric power to various electric circuits of the radiation imaging device 7 including the radiation detector 19. A radiation shielding member (not shown) made of lead or the like is provided under the top plate 13 and above the case 20, for the purpose of preventing damage to the electric circuits contained in the case 20 by radiation irradiation.

Figure 3:
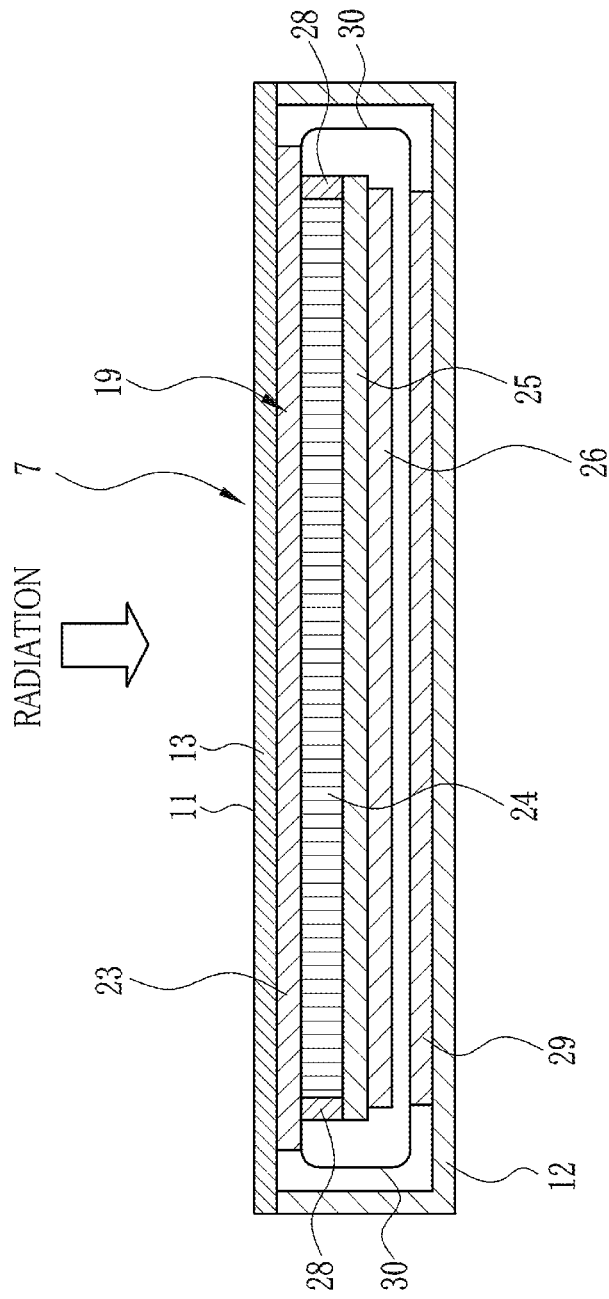
FIG. 3 is a schematic sectional view of the radiation imaging device.

The radiation detector 19 is constituted of a sensor panel 23, a scintillator panel 24, a reflective layer 25, and a radiation irradiation detecting photodetector 26 laminated in this order in a radiation incident direction. As shown in FIG. 3, the sensor panel 23 is glued on an entire rear surface of the top plate 13 with an adhesive. The scintillator panel 24 is enclosed with a sealant 28 to protect a scintillator 37 (see FIG. 4) from moisture and the like. A control board 29 is disposed on the bottom of the housing 12. The control board 29 is electrically connected to the sensor panel 23 through flexible cables 30.

Figure 4:
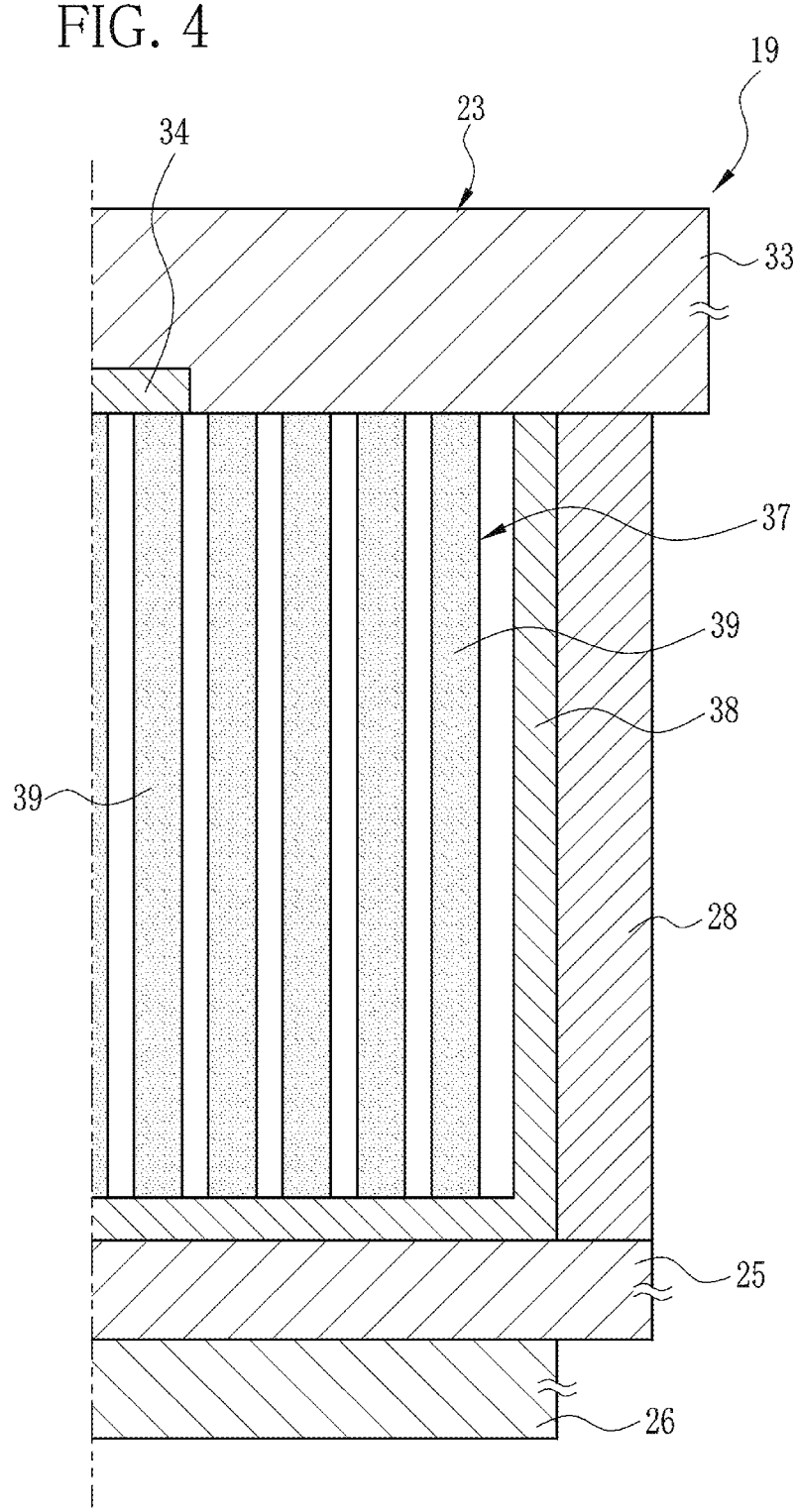
FIG. 4 is a sectional view of an end portion of a radiation detector.

FIG. 4 shows a cross section of the radiation detector 19 on its end portion. The sensor panel 23, which detects light radiating from the scintillator panel 24, includes a rectangular flat sensor substrate 33 and a photosensor 34 provided in a rear surface of the sensor substrate 33. The photosensor 34 is composed of a two-dimensional array of photoelectric converters each for converting the light radiating from the scintillator 37 into an electric signal. As the photoelectric converter, for example, a photodiode (PD) made of amorphous silicon (a-Si) is used. As the sensor substrate 33, a heat-resistant glass substrate is used, such that the photodiodes can be formed by evaporation of the amorphous silicon, for example. The thickness of the sensor substrate 33 is of the order of 700 μm, for example.

The scintillator panel 24 is constituted of the scintillator 37 and a protective film 38 for covering the outer periphery of the scintillator 37. The radiation transmitted through the body of the patient H is applied to the housing 12, and enters the scintillator 37 through the top plate 13 and the sensor panel 23. The scintillator 37 absorbs the radiation, and emits the light. As the scintillator 37, for example, CsI:Tl (cesium iodide doped with thallium), CsI:Na (cesium iodide activated with sodium), GOS ($Gd_2O_2S$:Tb), or the like is available in general. In this embodiment, by evaporation of the CsI:Tl onto the sensor substrate 33, a plurality of columnar crystals 39 are formed in the scintillator 37 along a light exit direction heading from the scintillator 37 to the sensor panel 23. Each columnar crystal 39 has a substantially uniform average diameter in its longitudinal direction.

The light produced by the scintillator 37 propagates through the columnar crystals 39 due to a light guide effect of the columnar crystals 39, and exits to the sensor panel 23. At this time, the columnar crystals 39 prevent the dispersion of the light exiting to the sensor panel 23, so a blur is reduced in a radiographic image detected by the radiation imaging device 7. The light that has reached the depths of the scintillator 37 is reflected from the reflective layer 25 to the sensor panel 23. This allows increase in a light amount to be incident upon the sensor panel 23, in other words, improvement in the detection efficiency of the light produced by the scintillator 37.

The filling rate of the CsI to the above scintillator 37 is confined to an appropriate range, and optimally of the order of 70 to 85%, for example, though it depends on the thickness of the scintillator 37. More specifically, when the filling rate of the CsI is too low (less than 70%), the light emission amount of the scintillator 37 is significantly reduced. When the filling rate of the CsI is too high (more than 85%), on the other hand, the adjacent columnar crystals come into contact with each other, if the thickness exceeds a certain level. Thus, optical crosstalk occurs among the columnar crystals. The occurrence of the optical crosstalk causes the difference between a pattern of a radiation amount entering the scintillator 37 and a pattern of a light amount exiting from the scintillator 37, and results in deterioration in accuracy of radiation detection (deterioration in sharpness of a detected image, when the applied radiation is detected as the image). For this reason, it is necessary to leave a gap of appropriate size between the adjacent columnar crystals, in order to secure the sensitivity and accuracy of the radiation detection.

The protective film 38 is made of a moisture-proof material, for example, an organic film manufactured by vapor phase polymerization such as a thermal CVD method or a plasma CVD method. As the organic film, a vapor-phase polymerized film formed of polyparaxylylene resin by the thermal CVD method, or a plasma polymerized film formed of plasma polymerized film unsaturated hydrocarbon monomer of fluorine-containing composite unsaturated hydrocarbon monomer. Alternatively, a lamination of the organic film and an inorganic film is usable. The inorganic film is preferably made of silicon nitride (SiNx), silicon oxide (SiOx), silicon oxynitride (SiOxNy), $Al_2O_3$, or the like.

In this embodiment, the radiation imaging device 7 adopts an irradiation side sampling (ISS) method, in which the sensor panel 23 is disposed on a radiation incident side of the scintillator panel 24. The light radiates more strongly from the radiation incident side of the scintillator 37. The distance between the sensor panel 23 and a light emission point of the scintillator 37 is shorter in the ISS method than that in a penetration side sampling (PSS) method, in which the sensor panel is disposed on a side opposite to the radiation incident side of the scintillator panel. Thus, adopting the ISS method increases resolution of the radiographic image. Also, increase in a light amount received by the sensor panel 23 results in improvement of the sensitivity of the radiation imaging device 7.

The reflective layer 25 has wavelength selectivity, in other words, specularly reflects a short wavelength component of the light produced by the scintillator 37 to the sensor panel 23, while transmitting a long wavelength component of the light therethrough. As the reflective layer 25, for example, a dichroic filter is used. The dichroic filter is resistant to heat and does not deteriorate with time, so does not cause degradation in radiographic image quality. The dichroic filter has higher light transmittance and sharper properties than those of a general color filter, and hence contributes to improvement of the radiographic image quality.

Figure 5:
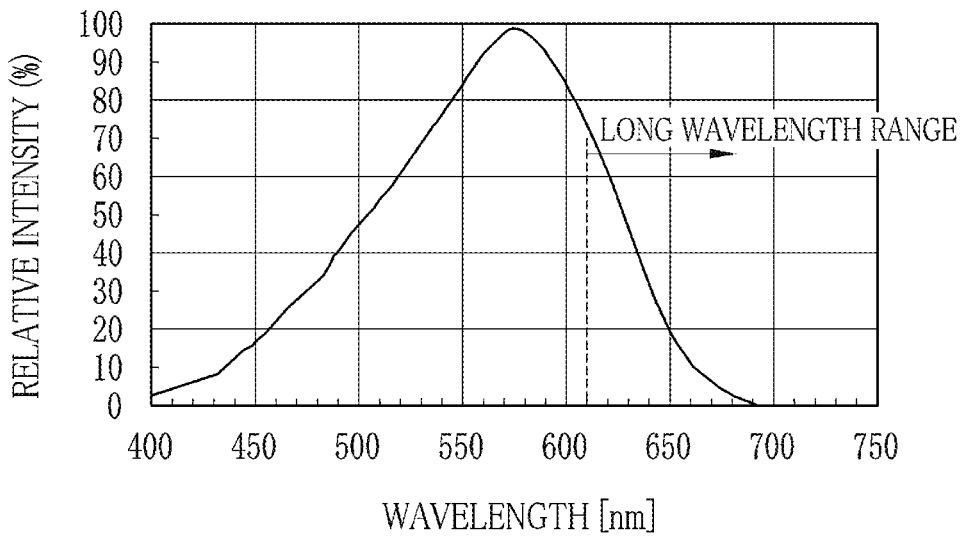
FIG. 5 is a graph showing a CsI:Tl emission spectrum.
Figure 6:
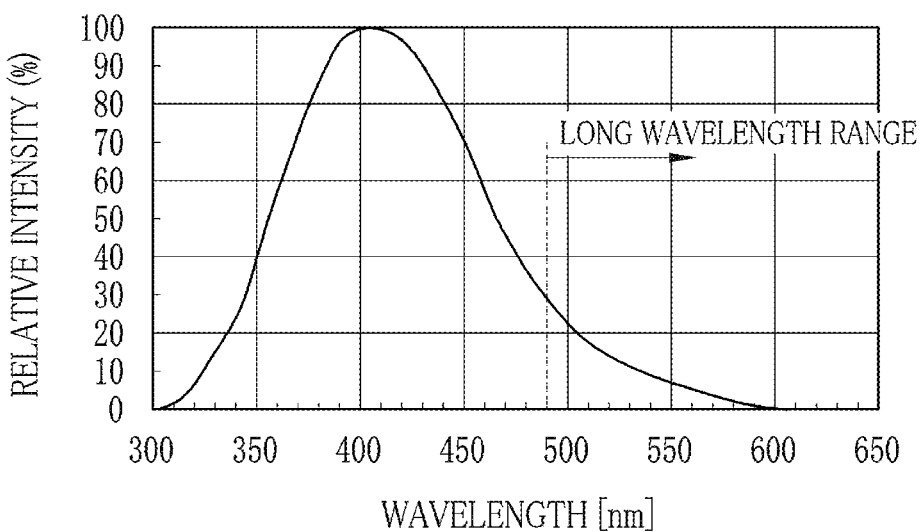
FIG. 6 is a graph showing a CsI:Na emission spectrum.

As shown in FIG. 5, light emitted from the CsI:Tl has a peak wavelength of approximately 565 nm and a broad wavelength band of 400 to 700 nm. When the scintillator 37 is made of the CsI:Tl, the reflective layer 25 preferably transmits the light in a wavelength band longer than the peak wavelength of 565 nm e.g. in a wavelength band of 620 nm or more, while reflecting to the sensor panel 23 the light in a wavelength band shorter than 620 nm. When the scintillator 37 is made of the CsI:Na, as shown in FIG. 6, the reflective layer 25 preferably transmits the light in a wavelength band longer than a peak wavelength (for example, around 400 nm) of the CsI:Na e.g. in a wavelength band of 480 nm or more, and reflects the light in a wavelength band shorter than 480 nm.

The scintillator 37 is evaporated onto the sensor panel 23, and the protective film 38 covers the scintillator 37. With adhesion of the protective film 38, the reflective layer 25 tightly adheres to the scintillator panel 24. In another case, the reflective layer 25 may be glued on the scintillator panel 24 with a light transparent adhesive.

Figure 7:
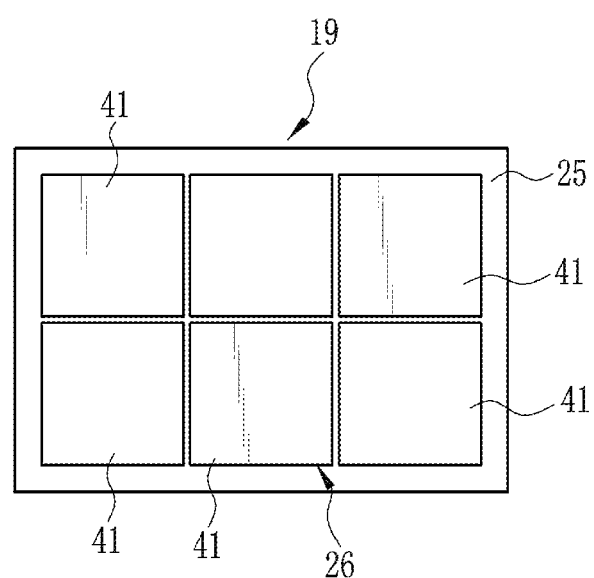
FIG. 7 is a plan view of a radiation irradiation detecting photodetector.

As shown in FIG. 7, the radiation irradiation detecting photodetector 26 is disposed on the reflective layer 25 on aside opposite to a side facing to the scintillator panel 24. The radiation irradiation detecting photodetector 26 is constituted of, for example, six photodetecting sections 41 arranged in a tiled manner. Each photodetecting section 41 detects the long wavelength component of the light that has transmitted through the reflective layer 25 and outputs a detection signal, in order to detect whether or not the radiation is emitted from the radiation generator 6. Upon the detection of radiation irradiation, the sensor panel 23 starts measuring the radiation. Since the detection signal from the photodetecting section 41 is not used for radiography, the size of each photodetecting section 41 is set larger than that of the single photoelectric converter of the sensor panel 23. The photodetecting sections 41 are glued on the reflective layer 25 with a light transparent adhesive, for example.

As the photodetecting section 41, a photodetector having a photoelectric conversion layer made of an organic photoelectric conversion material is preferably used. The photoelectric conversion layer can be formed by depositing the organic photoelectric conversion material on a substrate with the use of a liquid discharge head such as an inkjet head, so heat resistance is not required of the substrate. Thus, the photodetector using the photoelectric conversion layer of the organic photoelectric conversion material does not necessarily use a heat-resistant substrate e.g. a glass substrate with certain thickness, but is made thinner than a photodetector using a photoelectric conversion layer of a-Si or the like.

Figure 8:
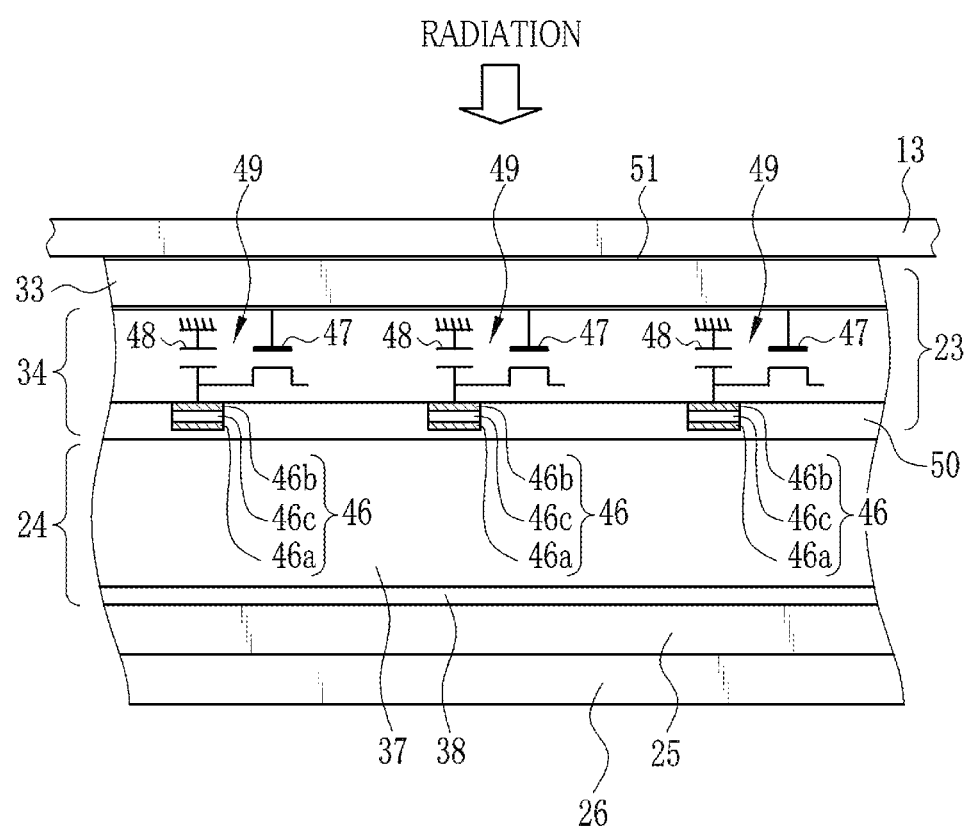
FIG. 8 is a sectional view of apart of the radiation imaging device that schematically shows the structure of photosensors.

Next, the photosensor 34 of the sensor panel 23 will be described. As shown in FIG. 8, the photosensor 34 includes plural pixel units 49 formed into a matrix on the sensor substrate 33. Each pixel unit 49 is constituted of a photoelectric converter (pixel) 46 formed of a photodiode (PD) and the like, a thin film transistor (TFT) 47, and a capacitor 48. A flattening layer 50 is formed on a surface of the sensor panel 23 on a side opposite to the radiation incident direction. As described above, the sensor panel 23 is glued on the rear surface of the top plate 13 with an adhesive layer 51.

The photoelectric converter 46 is constituted of a lower electrode 46a, an upper electrode 46b, and a photoelectric conversion layer 46c sandwiched between the lower and upper electrodes 46a and 46b. The photoelectric conversion layer 46c absorbs the light radiating from the scintillator 37, and produces electric charge the amount of which corresponds to the amount of the absorbed light. The lower electrode 46a is preferably made of a conductive material that is transparent to at least the wavelength of the light radiating from the scintillator 37. This is because the light from the scintillator 37 needs to be incident upon the photoelectric conversion layer 46c. More specifically, the lower electrode 46a is preferably made of transparent conducting oxide (TCO) that has high transmittance to visible light and low resistance.

A metal thin film such as Au may be used as the lower electrode 46a, but a resistance value of the metal thin film easily increases with increase in light transmittance to 90% or more. For this reason, the TCO is preferred. For example, ITO, IZO, AZO, FTO, $SnO_2$, $TiO_2$, $ZnO_2$, or the like is preferably used, and the ITO is the most preferable in view of process simplicity, low resistance, and high transparency. Note that, the lower electrode 46a of every pixel may be coupled and integrated into one unit, or may be divided from pixel to pixel.

The photoelectric conversion layer 46c is made of any material as long as the material absorbs the light and produces the electric charge, such as amorphous silicon, for example. The photoelectric conversion layer 46c made of the amorphous silicon can absorb the light radiating from the scintillator 37 in abroad wavelength band. Since the photoelectric conversion layer 46c of the amorphous silicon is formed by evaporation, a heat-resistant glass substrate is preferably used as the sensor substrate 33.

The TFT 47 is constituted of a lamination of a gate electrode, a gate insulating film, and an active layer (channel layer). A source electrode and a drain electrode are formed on the active layer with a predetermined gap therebetween. The active layer is made of any material out of amorphous silicon, amorphous oxide, an organic semiconducting material, a carbon nanotube, and the like, but the material for making the active layer is not limited to them.

Figure 9:
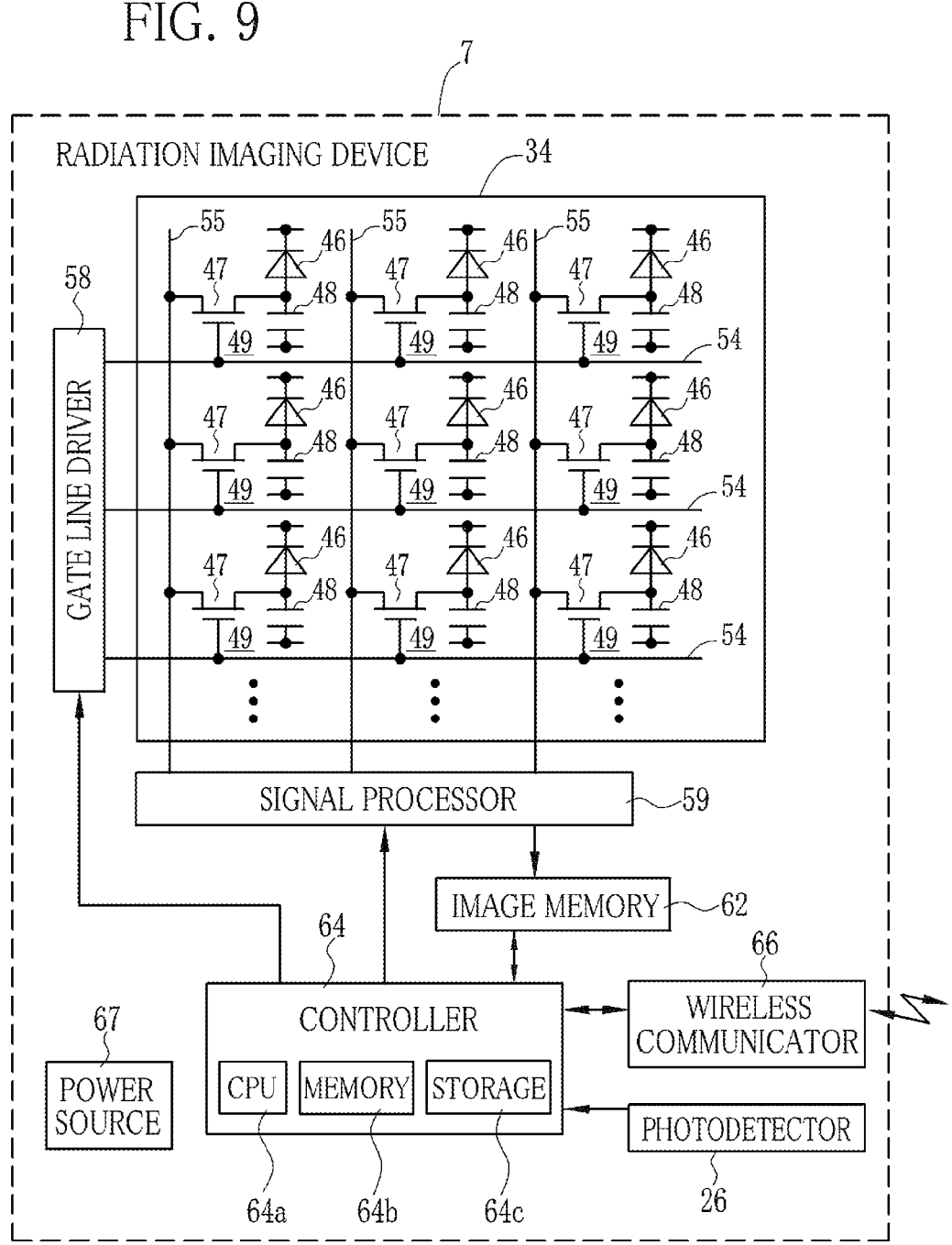
FIG. 9 is a block diagram showing the electrical structure of the radiation imaging device.

As shown in FIG. 9, photosensor 34 has plural gate lines 54 extending in a certain direction (row direction), and plural data lines 55 extending in a direction (column direction) intersecting with the above certain direction. The TFTs 47 are turned on or off on a row-by-row basis in response to a signal from the gate lines 54. When the TFT 47 is turned on, the electric charge accumulated in the capacitor 48 (and the middle between the lower electrode 46a and the upper electrode 46b of the photoelectric converter 46) is read out through the data lines 55.

Every gate line 54 of the sensor panel 23 is connected to a gate line driver 58, and every data line 55 is connected to a signal processor 59. When the radiation (radiation having image information of the body of the patient) transmitted through the body of the patient is incident upon the radiation imaging device 7, the scintillator 37 emits the light from a position corresponding to a radiation irradiation position of the radiation receiving surface 11 by an amount corresponding to a radiation irradiation amount of each radiation irradiation position. The photoelectric converter 46 of each individual pixel unit 49 produces the electric charge by an amount corresponding to the amount of the light radiating from the corresponding position of the scintillator 37. The electric charge is accumulated in the capacitor 48 (and the middle between the lower electrode 46a and the upper electrode 46b of the photoelectric converter 46) of each pixel unit 49.

After the electric charge is accumulated in the capacitor 48 of each pixel unit 49, as described above, the TFTs 47 of the pixel units 49 are successively turned on by the signal sent from the gate line driver 58 through the gate lines 54 on a row-by-row basis. The electric charge accumulated in the capacitors 48 of the pixel units 49 being turned on is transferred through the data lines 55 to the signal processor 59, as analog pixel signals. Thus, the electric charge accumulated in the capacitor 48 of every pixel unit 49 is successively read out on a row-by-row basis.

The signal processor 59 includes one amplifier and one sample holding circuit for each data line 55. The pixel signal transferred through each data line 55 is amplified by the amplifier, and then held by the sample holding circuit. An output of every sample holding circuit is connected to a multiplexer and an analog-to-digital converter (A/D). The pixel signal held by each sample holding circuit is successively inputted to the multiplexer in series, and is converted by the A/D into digital image data (image signal).

The signal processor 59 is connected to an image memory 62. The image data outputted from the A/D of the signal processor 59 is successively written to the image memory 62. The image memory 62 has a storage capacity of plural frames of the image data. Whenever the radiographic image is captured, the captured image data is stored to the image memory 62.

The image memory 62 is connected to a controller 64 for controlling the operation of the entire radiation imaging device 7. The controller 64, having a microcomputer, includes a CPU 64a, a memory 64b having a ROM and a RAM, and nonvolatile storage 64c such as a hard disk drive (HDD) or a flash memory.

The controller 64 is connected to a wireless communicator 66. The wireless communicator 66 is compatible with a wireless local area network (LAN) standard typified by IEEE 802.22a/b/g/n and the like. The wireless communicator 66 controls transmission of various types of information to/from external equipment through a wireless network. The controller 64 performs wireless communication with the console 8 (see FIG. 10) through the wireless communicator 66, to send and receive various types of information to and from the console 8.

The radiation imaging device 7 is provided with a power source 67. Various electric circuits described above (the gate line driver 58, the signal processor 59, the image memory 62, the wireless communicator 66, the controller 64, and the like) are operated by electric power supplied from the power source 67. The power source 67 contains the battery (secondary battery) described above, so as not to impair portability of the radiation imaging device 7, and supplies the electric power from the charged battery to the various electric circuits. The gate line driver 58, the signal processor 59, the image memory 62, the controller 64, and the power source 67 are contained in the case 20 or provided on the control board 29.

The controller 64 is connected to the radiation irradiation detecting photodetector 26. When the radiation generator 6 emits the radiation for radiography, the radiation irradiation detecting photodetector 26 produces the detection signal. In response to the detection signal, the controller 64 starts reset operation by which each photoelectric converter 46 is brought into a state ready for photoelectric conversion. In the reset operation, the gate line driver 58 turns on every TFT 47 of every pixel unit 49, and the electric charge accumulated in the capacitor 48 of every pixel unit 49 is discharged through the data lines 55. The reset operation removes dark current that is caused by electric charge remaining in the pixel units 49, electric charge trapped in a defect of the photoelectric converter 46, and the like. Immediately after the reset operation, each pixel unit 49 is put into a charge accumulation mode. In the charge accumulation mode, each pixel unit 49 performs photoelectric conversion of the light from the scintillator 37, and accumulates the converted electric charge.

Figure 10:
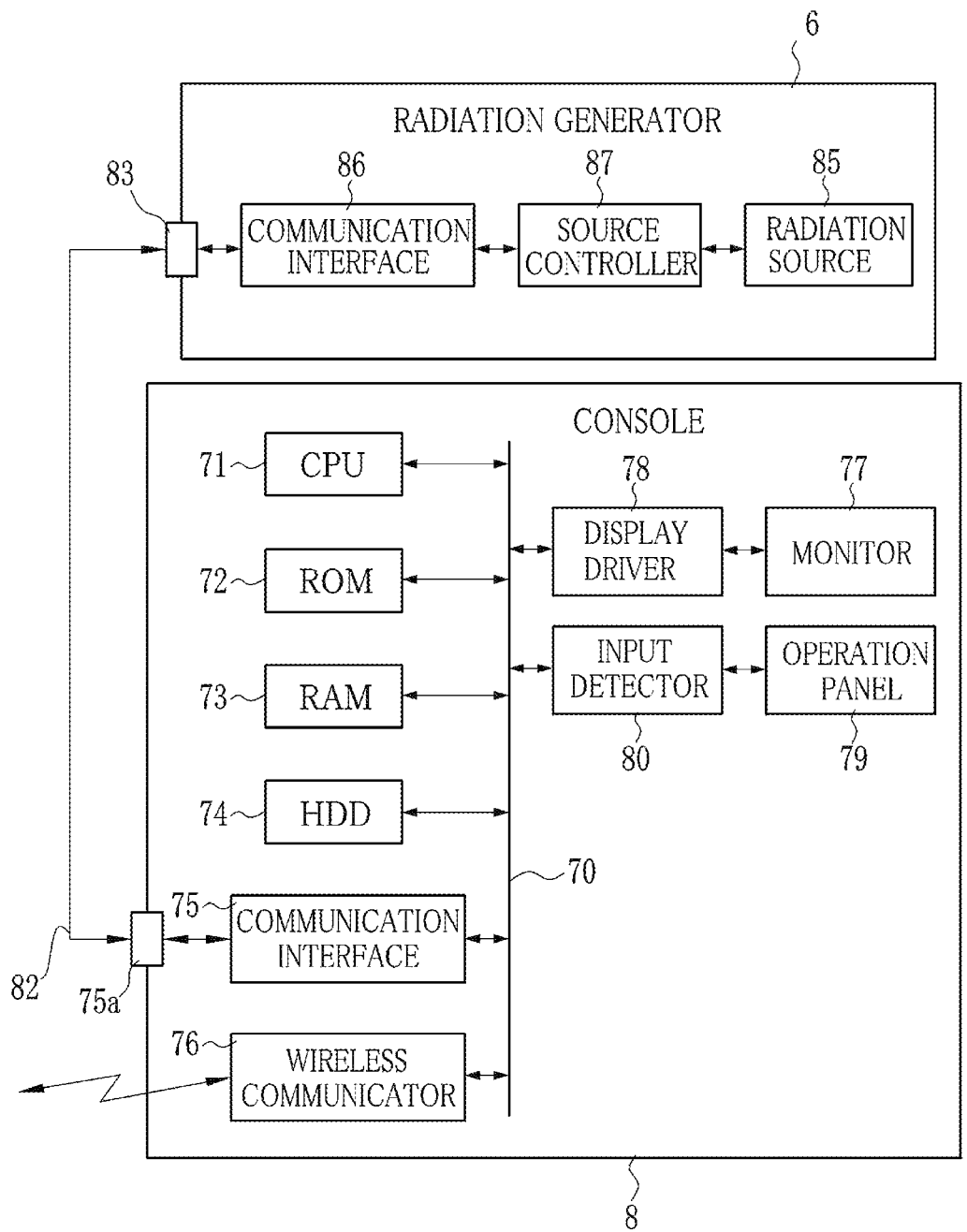
FIG. 10 is a block diagram showing the electrical structure of a console and a radiation generator.

As shown in FIG. 10, the console 8, composed of a computer, is provided with a CPU 71 for controlling the operation of the entire radiation imaging system 5, a ROM 72 for storing in advance various types of programs including a control program, a RAM 73 for temporarily storing various types of data, and a HDD 74 for storing various types of data. The CPU 71, the ROM 72, the RAM 73, and the HDD 74 are connected to each other through a bus 70. To the bus 70, a communication interface 75 and a wireless communicator 76 are connected. A monitor 77 is also connected to the bus 70 via a display driver 78, and an operation panel 79 is connected thereto via an input detector 80.

The communication interface 75 is connected to the radiation generator 6 through a connection terminal 75a, a communication cable 82, and a connection terminal 83 of the radiation generator 6. The CPU 71 sends and receives various types of information such as exposure conditions to and from the radiation generator 6 through the communication interface 75. The wireless communicator 76 has the function of performing the wireless communication with the wireless communicator 66 of the radiation imaging device 7. The CPU 71 sends and receives various types of information such as the image data to and from the radiation imaging device 7 through the wireless communicator 76. The display driver 78 produces and outputs a signal for displaying various types of information on the monitor 77, and the CPU 71 displays an operation menu, the captured radiographic image, and the like on the monitor 77 through the display driver 78. The operation panel 79 has plural keys or buttons. Various types of information and operation commands are inputted from the operation panel 79. The input detector 80 detects operation on the operation panel 79, and informs the CPU 71 of a detection result.

The radiation generator 6 is provided with a radiation source 85, a communication interface 86, and a source controller 87. The communication interface 86 sends and receives various types of information such as the exposure conditions to and from the console 8. The source controller 87 controls the radiation source 85 based on the exposure conditions (including information of tube voltage and tube current) received from the console 8.

Next, the operation of this embodiment will be described. In performing radiography using the radiation imaging device 7, a doctor or a radiologist disposes the radiation imaging device 7 between a body portion of the patient H to be imaged and an imaging table, such that the radiation receiving surface 11 faces upward, and adjusts the direction, position, and the like of the radiation imaging device 7 as a preparation.

When the preparation is completed, a start of radiography is commanded from the operation panel 79. Thus, the console 8 sends the command signal for commanding a start of exposure to the radiation generator 6, so the radiation generator 6 emits the radiation from the radiation source 85. The radiation from the radiation source 85 transmits through the body portion to be imaged, and is incident upon the radiation receiving surface 11 of the radiation imaging device 7. Then, the radiation enters the scintillator 37 through the top plate 13 and the sensor panel 23. The scintillator 37 absorbs the incident radiation, and emits the light the amount of which corresponds to the absorbed radiation irradiation amount.

Figure 11:
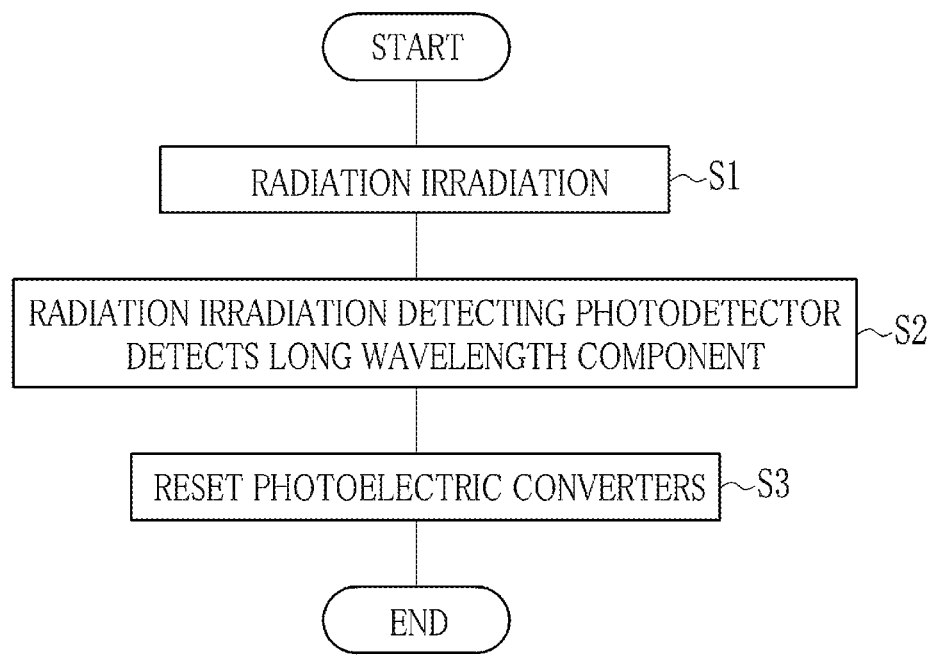
FIG. 11 is a flowchart showing a reset operation procedure of photoelectric converters.
Figure 12:
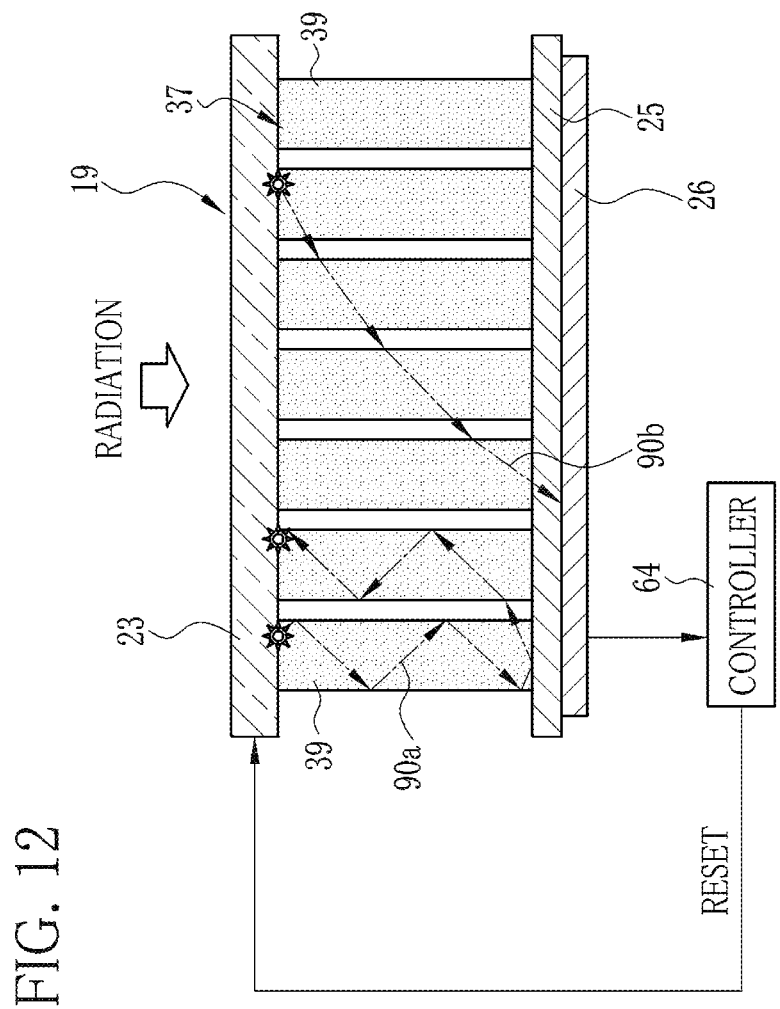
FIG. 12 is an explanatory view schematically showing a state where a short wavelength component of light produced by the scintillator is reflected, while a long wavelength component of the light is transmitted.

FIG. 11 shows a procedure of the reset operation of the photoelectric converters 46 triggered by radiation irradiation (S1) from the radiation generator 6. As shown in FIG. 12, which illustrates a part of the radiation detector 19, a long wavelength component 90b of the light radiating from the scintillator 37 transmits through the reflective layer 25, and is detected by the radiation irradiation detecting photodetector 26 (S2). The radiation irradiation detecting photodetector 26 sends the detection signal to the controller 64. The controller 64 resets each photoelectric converter 46 by control of the gate line driver 58 (S3). Thus, each photoelectric converter 46 is put into the charge accumulation mode, and starts detecting the light emitted from the scintillator 37.

The light from the scintillator 37 propagates through the columnar crystals 39 with total internal reflection to the sensor panel 23 or the reflective layer 25. The light that has reached the sensor panel 23 is detected by the photoelectric converters 46. Out of the light that has reached the reflective layer 25, the short wavelength component 90a is specularly reflected from the reflective layer 25, and is incident upon the sensor panel 23. This allows increase in the light amount detected by the sensor panel 23. The short wavelength component 90a has the relatively high refractive index. Thus, even if an incident angle with respect to the reflective layer 25 is less than the critical angle, the refracted light shortly has an incident angle of the critical angle or more. Therefore, the short wavelength component 90a of the light is incident upon the sensor panel 23 at a position near to a light radiating position in the scintillator 37.

The long wavelength component 90b having the lower refractive index than that of the short wavelength component 90a propagates from the light radiating position to the reflective layer 25, and transmits through the reflective layer 25. Accordingly, the long wavelength component 90b is not reflected from the reflective layer 25, and is not incident upon the sensor panel 23. This allows prevention of a blur in the radiographic image caused by the crosstalk of the long wavelength component 90b.

The sensor panel 23 detects the light applied to the pixel unit 49 as an image, and stores the image data to the image memory 62. The CPU 64a sends the image memory stored in the image memory 62 to the console 8. The CPU 71 of the console 8 stores the image data received from the radiation imaging device 7 through the RAM 73 to the HDD 74. The CPU 71 displays the radiographic image composed of the image data stored in the HDD 74 on the monitor 77 through the display driver 78.

According to the conventional radiation imaging system, the photoelectric converters were reset in synchronization with the radiation irradiation from the radiation generator. Thus, as shown in FIG. 1, the radiation generator 6 and the radiation imaging device 7 were connected with a cable 92, and the radiation generator 6 sends a timing signal to the radiation imaging device 7 through the cable 92 upon emitting the radiation. In this structure, the provision of the cable 92 deteriorates the handleability of the radiation imaging device 7. On the other hand, the present invention eliminates the need for providing the cable 92 connecting the radiation generator 6 to the radiation imaging device 7, and improves the handleability of the radiation imaging device 7. Also, in the conventional radiation imaging device, the long wavelength component of the light produced by the scintillator is uselessly absorbed by an absorption layer to prevent the blur of the radiation image. According to the present invention, the long wavelength component of the light is effectively usable for obtaining the reset timing of the photoelectric converters.

In the above embodiment, the reflective layer selectively performs reflection and transmission in accordance with the wavelength of the light produced by the scintillator 37, but may selectively perform reflection and transmission in accordance with the light incident angle, for example. In this case, for example, when the short wavelength component of the light propagates through the columnar crystal, the light incident angle of the short wavelength component with respect to the reflective layer is made equal to or more than the critical angle of the columnar crystal, so the short wavelength component is reflected from the reflective layer. On the other hand, the light incident angle of the long wavelength component with respect to the reflective layer is made less than the critical angle of the columnar crystal, so the long wavelength component is transmitted through the reflective layer. This structure can obtain the same effect as above.

Second Embodiment

Figure 13:
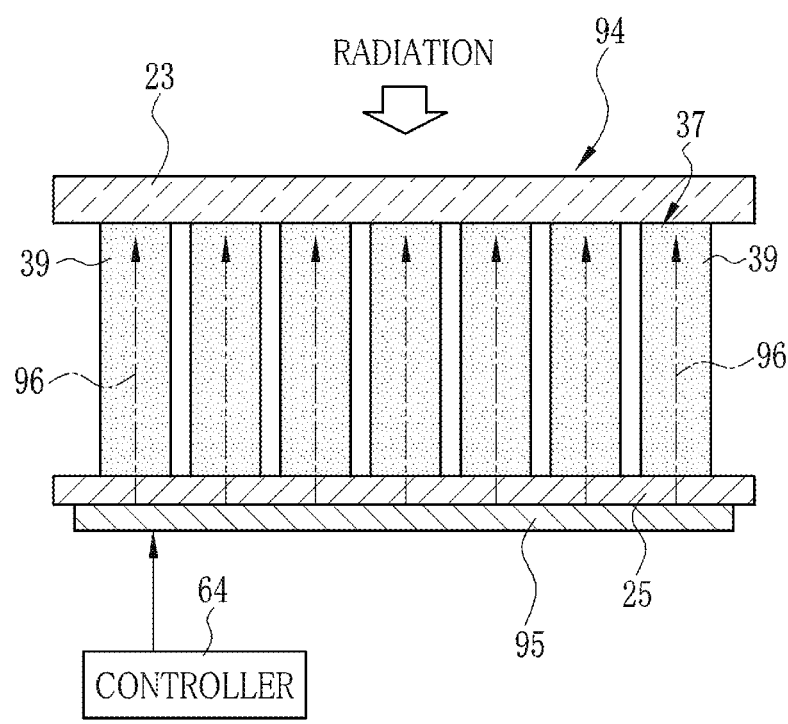
FIG. 13 is an explanatory view schematically showing a state of light reset of the photoelectric converters using a reset light source.

Next, a second embodiment of the present invention will be described. Note that, the same reference numerals refer to components same as or similar to those of the first embodiment, and description of the components is omitted. As shown in FIG. 13, in a radiation detector 94 of the second embodiment, a reset light source 95 is disposed on a light transmitting side of the reflective layer 25. The reset light source 95 emits reset light 96 in a long wavelength band. The reset light 96 is applied to the sensor panel 23 through the reflective layer 25 and the scintillator 37, in order to perform light reset of each photoelectric converter 46.

In the radiation imaging device using the sensor panel having the photoelectric converters, dark current occurs in general. The dark current is caused by a radiation irradiation history, a bias application history, residual charge remaining in the photoelectric converters without being transferred, charge trapped in a defect of an amorphous silicon film, and the like. If the dark current is constant, the image data is corrected to compensate for the dark current. However, the correction is difficult in the case of increasing the dark current due to deterioration in a characteristic of the photoelectric converters caused by an extended period of use. In the case of taking a motion image composed of plural frames during surgical operation, for example, increase in temperature of the amorphous silicon tends to cause release of the electric charge trapped in the defect, so the release of the electric charge occurs nonuniformly in an image area. Thus, the dark current of each frame becomes nonuniform, and the correction becomes difficult.

As a countermeasure against it, a technique called light reset is known. In this technique, the radiation imaging device is provided with the light source, and the reset light is applied from the light source to the photoelectric converters to improve the characteristic of the photoelectric converters. According to this technique, the application of the reset light forcefully produces the electric charge in the photoelectric converters to read out the produced charge not used as image information, or the electric charge is produced by an amount trapped in the defect to fill a defect level, so the dark current becomes uniform among the frames of the motion image. Therefore, the correction among the frames becomes easy.

As the reset light source 95, an EL element or an LED is usable. The light reset using the reset light source 95 is preferably performed, when a start of radiography is commanded with operation on the operation panel 79 of the console 8, and the console 8 sends a command signal for commanding a start of radiation irradiation to the radiation generator 6 and the radiation imaging device 7, for example.

As described in U.S. Pat. No. 5,905,772, the light reset of the photoelectric converters 46 made of the amorphous silicon preferably uses infrared light i.e. light in a long wavelength band. The reflective layer 25, which can transmit the light in the long wavelength band produced by the scintillator 37, also transmits the reset light 96 emitted from the reset light source 95. Thus, the reflective layer 95 does not interfere with the light reset. According to this embodiment, since the reset light source 95 can be disposed in a position not irradiated with the radiation, a malfunction of the reset light source 95 e.g. improper light emission caused by the radiation irradiation is prevented. Thus, this embodiment is preferably applicable to the radiation detector of the ISS method.

Third Embodiment

In the above first and second embodiments, one of the radiation irradiation detecting photodetector and the reset light source is disposed on the light transmitting side of the reflective layer. However, both of the radiation irradiation detecting photodetector and the reset light source may be disposed on the light transmitting side of the reflective layer. This allows obtainment of effects of both the first and second embodiments.

When the radiation irradiation detecting photodetector and the reset light source are disposed in this order under the reflective layer, the reset light emitted from the reset light source is absorbed by the radiation irradiation detecting photodetector. In consideration of it, if the reset light is set at a wavelength that is not absorbed by the radiation irradiation detecting photodetector, the reset light cannot transmit the reflective layer. On the contrary, when the reset light source and the radiation irradiation detecting photodetector are disposed in this order under the reflective layer, the reset light source can apply the reset light, and the radiation irradiation detecting photodetector can perform the light detection. However, the reset light source blocks the long wavelength component of the light transmitted through the reflective layer, and hence reduces the sensitivity of detecting the radiation irradiation.

Figure 14:
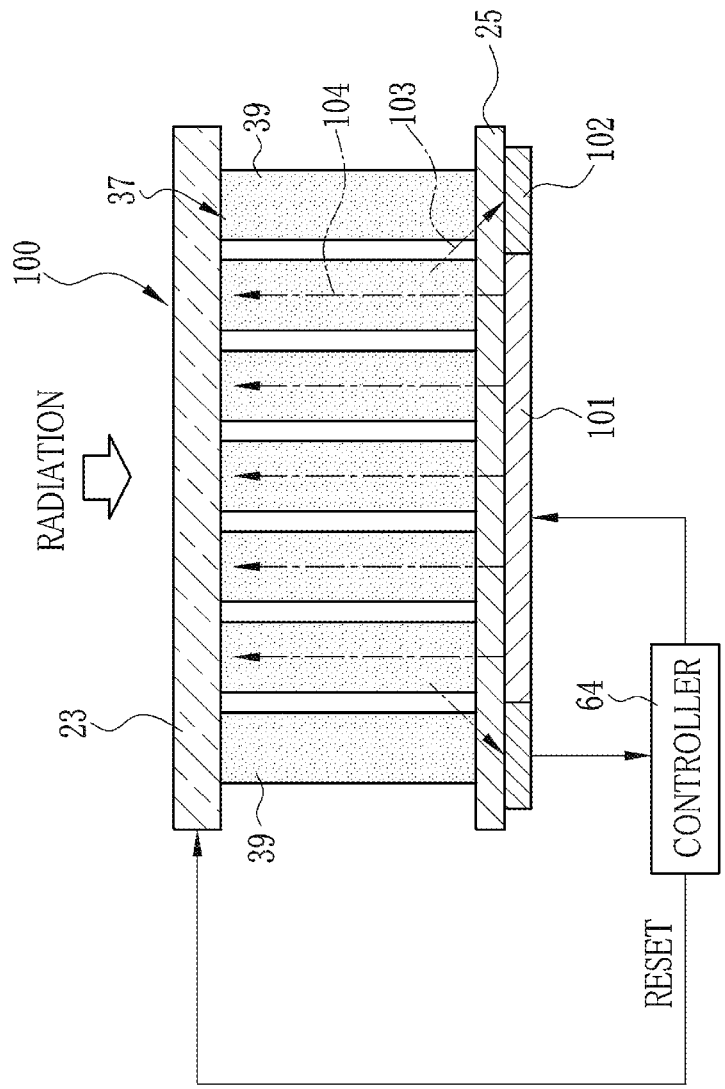
FIG. 14 is an explanatory view schematically showing a state where the reset light source and a radiation irradiation detecting photodetector are arranged in a tiled manner under the reflective layer.
Figure 15:
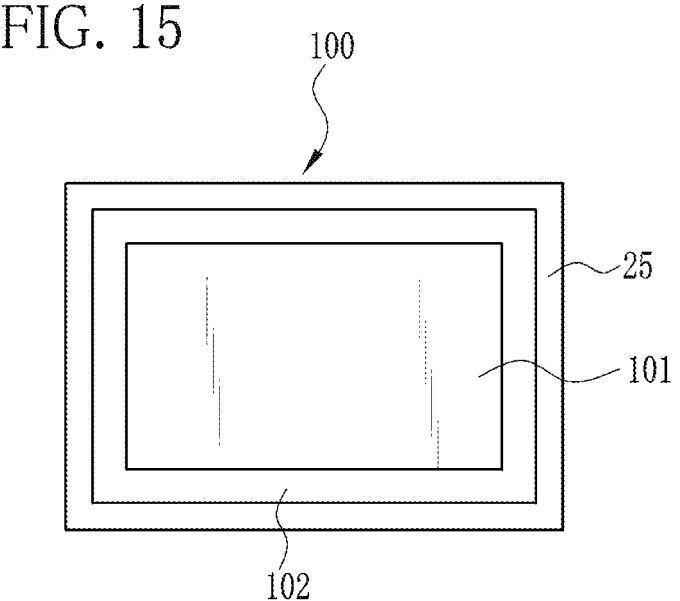
FIG. 15 is a plan view of the reset light source and the radiation irradiation detecting photodetector arranged under the reflective layer.

In a radiation detector 100 according to this embodiment, as shown in FIGS. 14 and 15, a reset light source 101 the size of the entire photoelectric converters 46 of the sensor panel 23 is disposed in such a position as to face to every photoelectric converter 46, and a radiation irradiation detecting photodetector 102 is disposed around the reset light source 101. The reset light source 101 applies the reset light including the long wavelength component to the photoelectric converters 46 through the reflective layer 25 and the scintillator 37. Thus, it is possible to certainly apply the reset light to every photoelectric converter 46 of the sensor panel 23. The radiation is certainly applied to an area larger than the image area in general, so the radiation irradiation detecting photodetector 102 disposed around the reset light source 101 can certainly detect the start of radiation irradiation.

As with the radiation irradiation detecting photodetector 26 of the first embodiment, the radiation irradiation detecting photodetector 102 is constituted of one or plural photodetecting sections having a photoelectric conversion layer made of an organic photoelectric conversion material. The radiation irradiation detecting photodetector 26 detects a long wavelength component of light 103 transmitted through the reflective layer 25 and outputs a detection signal, for the purpose of detecting the start of radiation irradiation from the radiation generator 6.

Upon input of the detection signal from the radiation irradiation detecting photodetector 102, the controller 64 makes the reset light source 101, being an EL element or an LED, apply reset light 104 in a long wavelength band to the photoelectric converters 46 of the sensor panel 23 for the light reset. The controller 64 also turns on the TFT 47 of every pixel unit 49 through the gate line driver 58, and ejects electric charge accumulated in the capacitor 48 of every pixel unit 49 through the data lines 55. This reset operation triggers a shift of each photoelectric converter 46 into a charge accumulation mode.

In this embodiment, the radiation irradiation detecting photodetector 102 is disposed around the reset light source 101, but a layout other than the third embodiment is adoptable as long as the reset light source 101 can perform the light reset of every photoelectric converter 46 in the sensor panel 23, and the radiation irradiation detecting photodetector 102 can detect the radiation irradiation without reduced detection sensitivity.

Fourth Embodiment

Figure 16:
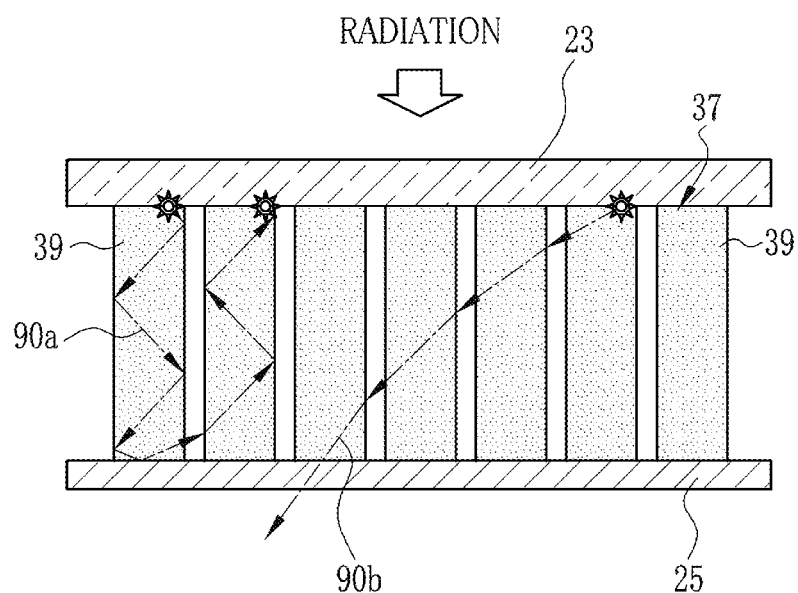
FIG. 16 is an explanatory view schematically showing a state where the long wavelength component of the light produced by the scintillator is transmitted through the reflective layer.
Figure 17:
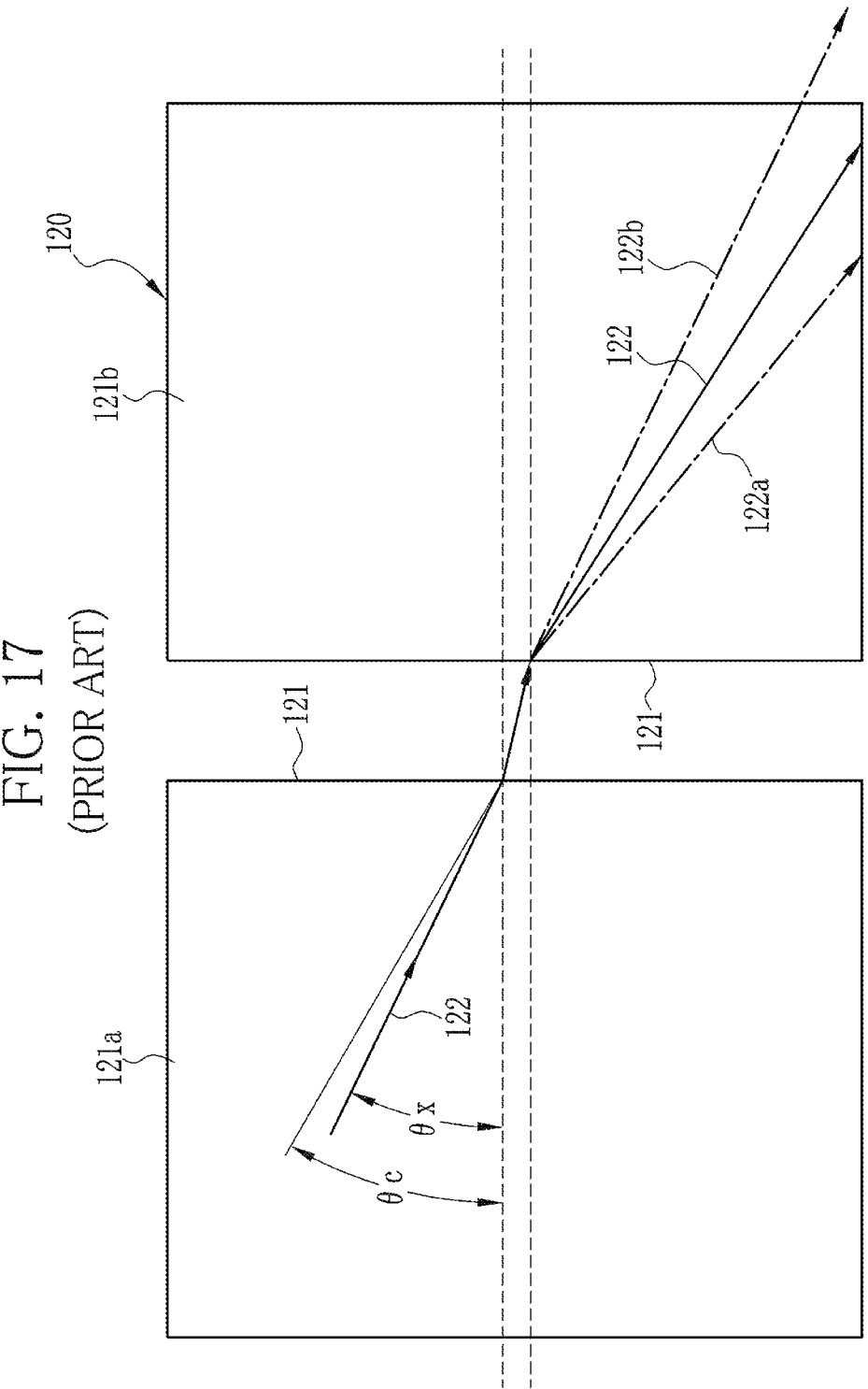
FIG. 17 is an explanatory view schematically showing a conventional optical path in the scintillator.
Figure 18:
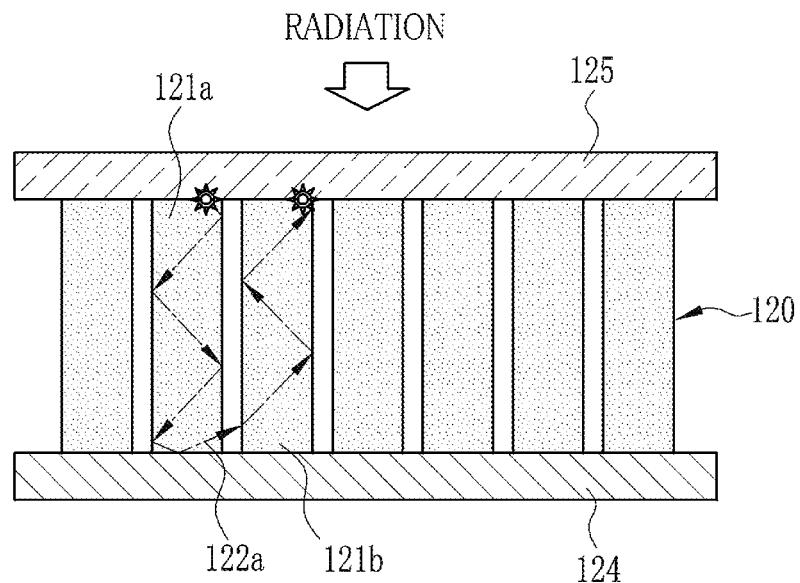
FIG. 18 is an explanatory view that schematically shows an optical path of the short wavelength component specularly reflected from the reflective layer.
Figure 19:
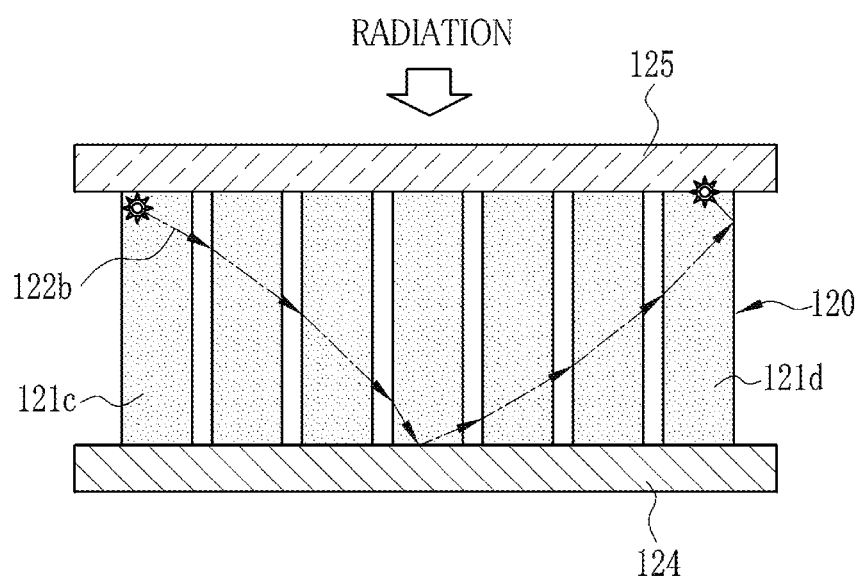
FIG. 19 is an explanatory view that schematically shows an optical path of the long wavelength component specularly reflected from the reflective layer.

In the first and second embodiments, the radiation irradiation detecting photodetector 26 or the reset light source 95 is disposed on the light transmitting side of the reflective layer 25, but as shown in FIG. 16, nothing may be disposed on the light transmitting side of the reflective layer 25. In this case, the long wavelength component of the light applied to the reflective layer 25 is transmitted as is. Also in this structure, the long wavelength component 90b is not reflected from the reflective layer 25 and does not enter the sensor panel 23. Thus, a blur of the radiographic image caused by the crosstalk of the long wavelength component 90b can be reduced. This structure eliminates the need for providing the conventional absorption layer, which absorbs the long wavelength component 90b.

Fifth Embodiment

In the above embodiments, the photoelectric conversion layer 46c of the photodetecting section 46 is made of amorphous silicon, but may be made of a material including an organic photoelectric conversion material. In this case, an absorption spectrum shows its peak mainly in a visible light range, and the photoelectric conversion layer 46c hardly absorbs an electromagnetic wave except for the light radiating from the scintillator 37. Thus, it is possible to prevent the occurrence of noise caused by absorption of the radiation such as the X-rays or γ-rays by the photoelectric conversion layer 46c. The photoelectric conversion layer 46c made of the organic photoelectric conversion material can be formed by adhesion of the organic photoelectric conversion material on the sensor substrate 33 using the liquid discharge head such as the inkjet head, so heat resistance is not required of the substrate 33. Thus, the sensor substrate 33 may be made of a material other than glass.

When the photoelectric conversion layer 46c is made of the organic photoelectric conversion material, the photoelectric conversion layer 46c hardly absorbs the radiation. Thus, in the radiation detector of the ISS method, it is possible to minimize attenuation of the radiation transmitting through the sensor panel 23, and hence reduction of radiation sensitivity. For this reason, making the photoelectric conversion layer 46c of the organic photoelectric conversion material is suitable in particular for the ISS method.

It is preferable that an absorption peak wavelength of the organic photoelectric conversion material for making the photoelectric conversion layer 46c is as near as possible to an emission peak of the scintillator 37, for the purpose of most efficiently absorbing the light radiating from the scintillator 37. The absorption peak wavelength of the organic photoelectric conversion material ideally coincides with the emission peak wavelength of the scintillator 37, but if not, the less the difference therebetween, the more light is absorbed. To be more specific, the difference between the absorption peak wavelength of the organic photoelectric conversion material of the photoelectric conversion layer 46c and the emission peak wavelength of the scintillator 37 by application of the radiation is preferably 10 nm or less, and more preferably 5 nm or less.

As the organic photoelectric conversion material satisfying such a condition, there are quinacridone organic compounds and phthalocyanine organic compounds, for example. Since the absorption peak wavelength of quinacridone in the visible light range is 560 nm, using the quinacridone as the organic photoelectric conversion material and using CsI(Tl) as a material of the scintillator 37 make it possible to restrain the difference between the peak wavelengths within 5 nm, and produce an approximately maximum amount of electric charge in the photoelectric conversion layer 46c.

The photoelectric conversion layer 46c applicable to the sensor panel 23 will be concretely described. In the sensor panel 23, an electromagnetic wave absorption and photoelectric conversion portion is constituted of organic layers including the electrodes 46a and 46b and the photoelectric conversion layer 46c sandwiched between the electrodes 46a and 46b (see FIG. 8). This organic layers are specifically composed of an electromagnetic wave absorbing portion, a photoelectric conversion portion, an electron transport portion, a hole transport portion, an electron blocking portion, a hole blocking portion, a crystallization preventing portion, electrodes, an interlayer contact improving portion, and the like that are stacked or mixed.

The above organic layer preferably contains an organic p-type compound or an organic n-type compound. An organic p-type semiconductor (compound) is a donor organic semiconductor (compound) mainly typified by a hole transport organic compound, and has the property of affording electrons. In more detail, when two types of organic materials are used in contact with each other, the organic p-type semiconductor (compound) is an organic compound having less ionization potential. Accordingly, any organic compound is available as the donor organic compound as long as the organic compound can produce the electrons. An organic n-type semiconductor (compound) is an acceptor organic semiconductor (compound) mainly typified by an electron transport organic compound, and has the property of accepting the electrons. To be more specific, when two types of organic materials are used in contact with each other, the organic n-type semiconductor (compound) is an organic compound having more electron affinity. Therefore, any organic compound is usable as the acceptor organic compound as long as the organic compound has electron receptivity.

Materials usable as the organic p-type semiconductor and the organic n-type semiconductor and the structure of the photoelectric conversion layer 46c are described in U.S. Pat. No. 7,847,258 corresponding to Japanese Patent Laid-Open Publication No. 2009-32854 in detail, so description thereof will be omitted.

The photoelectric converter 46 may have any structure as long as it includes at least a pair of electrodes 46a and 46b and the photoelectric conversion layer 46c, but preferably has one of an electron blocking layer and a hole blocking layer, and more preferably has both.

The electron blocking layer can be provided between the upper electrode 46b and the photoelectric conversion layer 46c. When bias voltage is applied between the upper electrode 46b and the lower electrode 46a, the electron blocking layer prevents increase of the dark current by infusion of electrons from the upper electrode 46b to the photoelectric conversion layer 46c. An electron donating organic material is used as the electron blocking layer. The concrete material of the electron blocking layer is chosen in accordance with the materials of the adjoining electrode and the adjoining photoelectric conversion layer 46c, and preferably has an electron affinity (Ea) by 1.3 eV or more larger than the work function (Wf) of the material of the adjoining electrode, and preferably has an ionization potential (Ip) equal to or less than the Ip of the material of the adjoining photoelectric conversion layer 46c. The materials usable as the electron donating organic material are described in the U.S. Pat. No. 7,847,258 in detail, and the description thereof will be omitted.

The thickness of the electron blocking layer is preferably 10 nm or more and 200 nm or less, more preferably 30 nm or more and 150 nm or less, most preferably 50 nm or more and 100 nm or less, in order to certainly bring out the dark current restriction effect and prevent reduction of the photoelectric conversion effect of the photoelectric converter 46.

The hole blocking layer can be provided between the photoelectric conversion layer 46c and the lower electrode 46a. When bias voltage is applied between the upper electrode 46b and the lower electrode 46a, the hole blocking layer prevents increase of the dark current by infusion of holes from the lower electrode 46a to the photoelectric conversion layer 46c. An electron accepting organic material is used as the hole blocking layer. The concrete material of the hole blocking layer is chosen in accordance with the materials of the adjoining electrode and the adjoining photoelectric conversion layer 46c, and preferably has an ionization potential (Ip) by 1.3 eV or more larger than the work function (Wf) of the material of the adjoining electrode, and preferably has an electron affinity (Ea) equal to or larger than the Ea of the material of the adjoining photoelectric conversion layer 46c. The materials usable as the electron accepting organic material are described in the U.S. Pat. No. 7,847,258 in detail, and the description thereof will be omitted.

The thickness of the hole blocking layer is preferably 10 nm or more and 200 nm or less, more preferably 30 nm or more and 150 nm or less, most preferably 50 nm or more and 100 nm or less, in order to certainly bring out the dark current restriction effect and prevent reduction of the photoelectric conversion effect of the photoelectric converter 46.

Note that, if the positions of the electronic blocking layer and the hole blocking layer are reversed, the bias voltage is applied such that the holes of the electric charge produced in the photoelectric conversion layer 46c move to the lower electrode 46a, and the electrons move to the upper electrode 46b. Both the electron blocking layer and the hole blocking layer are not necessarily provided. Providing one of the electron blocking layer and the hole blocking layer allows obtainment of a certain degree of the dark current restriction effect.

As the amorphous oxide for forming the active layer of the TFT 47, oxides (for example, In—O oxide) containing at least one of In, Ga, and Zn are preferable, and oxides (for example, In—Zn—O oxide, In—Ga—O oxide, and Ga—Zn—O oxide) containing at least two of In, Ga, and Zn are more preferable, and oxides containing all of In, Ga, and Zn are most preferable. As In—Ga—Zn—O amorphous oxide, an amorphous oxide of a composition represented by $InGaO_3$ $(ZnO)m$ (m represents natural number less than 6) in a crystalline state is preferable, and especially, $InGaZnO_4$ is more preferable. Note that, the amorphous oxide for forming the active layer is not limited to above.

An organic semiconducting material for forming the active layer includes a phthalocyanine compound, pentacene, vanadyl phthalocyanine, or the like, but is not limited to them. The composition of the phthalocyanine compound is described in U.S. Pat. No. 7,768,002 corresponding to the Japanese Patent Laid-Open Publication No. 2009-212389 in detail, so the description thereof will be omitted.

Forming the active layer of the TFT 47 out of one of the amorphous oxides, the organic semiconducting material, a carbon nanotube, and the like can effectively restrict the occurrence of noise, because these materials do not or hardly absorb radiation such as the X-rays.

Forming the active layer of the carbon nanotube can accelerate the switching speed of the TFT 47, and reduce the degree of absorption of light in the visible light range by the TFT 47. When the active layer is formed of the carbon nanotube, the performance of the TFT 47 significantly degrades only by mixture of a slight amount of metal impurity into the active layer. Thus, it is necessary to isolate and extract the carbon nanotube of extremely high purity by centrifugation, for use in the formation of the active layer.

Any of the film of the organic photoelectric conversion material and the film of organic semiconducting material has sufficient flexibility. Thus, a combination of the photoelectric conversion layer 46c made of the organic photoelectric conversion material and the TFT 47 having the active layer made of the organic semiconducting material does not necessarily require high stiffness of the sensor panel 23 to which the weight of the patient is applied as a load.

The sensor substrate 33 can be made of any material as long as it is light transparent and has low radiation absorptivity. Both the amorphous oxide for making the active layer of the TFT 47 and the organic photoelectric conversion material for making the photoelectric conversion layer 46c of the photoelectric converter 46 can be deposited at low temperature. Thus, the sensor substrate 33 can be made of not only a heat-resistant material such as semiconductor, quartz, and glass, but also flexible plastic, aramid, and bio-nanofiber. To be more specific, a flexible substrate made of polyester including polyethylene terephthalate, polybutylene phthalate, or polyethylene naphthalate, polystyrene, polycarbonate, polyether sulfone, polyalirate, polyimid, polycycloolefin, norbornene resin, poly(chlorotrifluoroethylene), or the like is available. Using the flexible substrate made of the plastic contribute to weight reduction and ease of portability. Note that, the sensor substrate 33 may be provided with an insulating layer for securing insulation, a gas barrier layer for preventing transmission of moisture and oxygen, an undercoat layer for improving flatness and adhesion to the electrode, and the like.

Since the aramid can be subjected to high temperature process of 200° C. or more, a transparent electrode material can be cured at high temperature with reduction of resistance therein, and automatic mounting of a driver IC including a reflow soldering can be performed. The aramid has a thermal expansion coefficient close to those of ITO (indium tin oxide) and the glass substrate, and hence is hard to warp and crack after manufacture. The aramid substrate can be thinner than the glass substrate. Note that, to form the sensor substrate 33, an ultra-slim glass substrate may be laminated with aramid.

The bio-nanofiber is a complex of a cellulose microfibril bundle (bacterial cellulose) produced by bacteria (acetobacter xylinum) and transparent resin. The cellulose microfibril bundle has a width of 50 nm, being one-tenth of the wavelength of the visible light, and high strength, high elasticity, and low thermal expansion. Impregnating the transparent resin such as acrylic resin or epoxy resin to the bacterial cellulose and hardening it make it possible to obtain the bio-nanofiber that contains fiber at 60 to 70% and has light transmittance of approximately 90% at a wavelength of 500 nm. The bio-nanofiber has a low thermal expansion coefficient (3 to 7 ppm) comparable to a silicon crystal, high strength (460 MPa) comparable to steel, high elasticity (30 GPa), and flexibility. Therefore, the sensor substrate 33 of the bio-nanofiber can be thinner than that of the glass.

When the glass substrate is used as the sensor substrate 33, the thickness of the entire sensor panel 23 is of the order of 0.7 mm, for example. On the other hand, through the use of a thin substrate made of the light transparent plastic as the sensor substrate 33, the thickness of the entire sensor panel 23 can be thinned to the order of 0.1 mm, for example, and the sensor panel 23 is made flexible. The flexibility of the sensor panel 23 improves impact resistance of the radiation imaging device 7, so the radiation imaging device 7 becomes hard to break. Any of the plastic resin, the aramid, the bio-nanofiber, and the like hardly absorbs the radiation. Thus, when the sensor substrate 33 is formed of these materials, the sensor substrate 33 hardly absorbs the radiation. Therefore, even in the ISS method in which the radiation transmits through the sensor panel 23, sensitivity to the radiation is not degraded.

As the photosensor 34, a CMOS sensor or an organic CMOS sensor that uses the organic photoelectric conversion material in the photoelectric converters (photodiodes) may be used. The CMOS sensor or the organic CMOS sensor, which use single crystalline silicon in its substrate, have faster carrier mobility by three to four digits than that of the photoelectric converters of the amorphous silicon, and have high radiation transmittance. Thus, the CMOS sensor or the organic CMOS sensor is suitably used in the radiation detector of the ISS method. Note that, the organic CMOS sensor is described in detail in United States Patent Application Publication No. 2009/224162 corresponding to Japanese Patent Laid-Open Publication No. 2009-212377, so detailed description thereof will be omitted.

To impart flexibility to the CMOS sensor or the organic CMOS sensor, the CMOS sensor or the organic CMOS sensor may be made of organic thin film transistors formed on a plastic film. The organic thin film transistor is described in detail in Tsuyoshi SEKITANI et al. "Flexible organic transistors and circuits with extreme bending stability" published in Nature Materials 9 on Nov. 7, 2010 on pages 1015-1022, so detailed description thereof will be omitted.

To impart flexibility to the CMOS sensor or the organic CMOS sensor, the photodiodes and the transistors made of single crystalline silicon may be laid out on a flexible plastic substrate. To lay out the photodiodes and the transistors on the plastic substrate, for example, a fluidic self-assembly (FSA) method is available in which device blocks of the order of several tens of micrometers are dispersed in a solution to lay out the device blocks in necessary arbitrary positions on the substrate. Note that, the FSA method is described in detail in Koichi MAEZAWA et al. "Fabrication of Resonant Tunneling Device Blocks for Fluidic Self-Assembly" IEICE Technical Report, Vol. 108, No. 87, pages 67-72, June 2008, so detailed description thereof will be omitted.

In the above embodiments, the present invention is applied to the radiation detector using the scintillator made of the columnar crystals, but is applicable to another radiation detector using another type of scintillator. The present invention is applied to the radiation detector of the ISS method, but is applicable to a radiation detector of the PSS method. The radiation detector is contained in the housing of the radiation imaging device of the cassette size, but may be mounted on any imaging device such as an upright type or a bed type, or in a mammography device. The radiation is not limited to the X-rays, but may be another type of radiation such as α-rays.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. A radiation imaging device comprising:
    a scintillator for converting applied radiation into light;
    a sensor panel disposed on a light exit side of said scintillator, said sensor panel having a two-dimensional array of photoelectric converters each for converting said light into an electric signal; and
    a reflective layer disposed on said scintillator on a side opposite to said light exit side, for reflecting a short wavelength component of said light to said sensor panel, while transmitting a long wavelength component of said light,
    wherein said sensor panel, said scintillator and said reflective layer are disposed from an upstream side in a radiation incident direction.

2. The radiation imaging device according to claim 1, wherein said light is reflected or transmitted selectively in accordance with a wavelength of said light.

3. The radiation imaging device according to claim 2, wherein said reflective layer is a dichroic filter.

4. The radiation imaging device according to claim 1, further comprising a protective film for covering an outer periphery of said scintillator, said protective film holding said reflective layer such that said reflective layer tightly contacts said scintillator.

5. The radiation imaging device according to claim 1, further comprising:
    a radiation irradiation detecting photodetector for detecting said long wavelength component transmitted through said reflective layer; and
    a controller for resetting all of said photoelectric converters of said sensor panel based on detection of said long wavelength component.

6. The radiation imaging device according to claim 5, wherein said radiation irradiation detecting photodetector is made of an organic photoelectric conversion material.

7. The radiation imaging device according to claim 5, wherein
    said radiation irradiation detecting photodetector includes a plurality of photodetecting sections arranged on said reflective layer; and
    each of said photodetecting sections has a detection area larger than one of said photoelectric converters of said sensor panel.

8. The radiation imaging device according to claim 5, further comprising a reset light source for applying reset light in a long wavelength to said photoelectric converters of said sensor panel through said reflective layer and said scintillator, said reset light source and said radiation irradiation detecting photodetector being disposed in a tiled manner on said reflective layer on a side opposite to a side facing to said scintillator.

9. The radiation imaging device according to claim 8, wherein said radiation irradiation detecting photodetector and said reset light source are glued on said reflective layer with a transparent adhesive.

10. The radiation imaging device according to claim 9, wherein
said reset light source has such a size as to cover all of said photoelectric converters of said sensor panel, and is disposed in such a position as to be opposed to all of said photoelectric converters of said sensor panel; and
said radiation irradiation detecting photodetector is disposed around said reset light source.

11. The radiation imaging device according to claim 1, further comprising a reset light source for applying reset light of a long wavelength to said photoelectric converters of said sensor panel through said reflective layer and said scintillator.

12. The radiation imaging device according to claim 1, wherein said radiation enters said scintillator through said sensor panel.

13. The radiation imaging device according to claim 12, wherein said long wavelength component of said light has a wavelength longer than an emission peak wavelength of said scintillator.

14. The radiation imaging device according to claim 13, wherein said scintillator is composed of a plurality of erected columnar crystals.

15. The radiation imaging device according to claim 14, wherein said scintillator is made of cesium iodide.

16. The radiation imaging device according to claim 15, wherein a filling rate of said cesium iodide to said scintillator is 70 to 85%.

17. The radiation imaging device according to claim 1, wherein said photoelectric converter has an organic photoelectric conversion film.

18. A radiation imaging system comprising:
a radiation generator for generating radiation; and
a radiation imaging device for imaging said radiation, including:
a scintillator for converting said radiation into light;
a sensor panel disposed on a light exit side of said scintillator, said sensor panel having a two-dimensional array of photoelectric converters each for converting said light into an electric signal;
a reflective layer disposed on said scintillator on a side opposite to said light exit side, for reflecting a short wavelength component of said light to said sensor panel, and transmitting a long wavelength component of said light;
a radiation irradiation detecting photodetector for detecting said long wavelength component transmitted through said reflective layer and issuing a detection signal; and
a controller for resetting all of said photoelectric converters of said sensor panel based on said detection signal,
wherein said sensor panel, said scintillator and said reflective layer are disposed from an upstream side in a radiation incident direction.

19. The radiation imaging system according to claim 18, wherein said radiation imaging device further includes a reset light source provided on said reflective layer with adjoining said radiation irradiation detecting photodetector, for applying reset light of a long wavelength to said photoelectric converters of said sensor panel.

20. A radiation imaging method comprising the steps of:
converting incident radiation into light by a scintillator;
entering said light into a reflective layer to make a short wavelength component of said light reflected to a sensor panel, while making a long wavelength component of said light transmitted through said reflective layer;
detecting said long wavelength component transmitted through said reflective layer; and
resetting all photoelectric converters provided in said sensor panel in response to the detection of said long wavelength component,
wherein said sensor panel, said scintillator and said reflective layer are disposed from an upstream side in a radiation incident direction.

* * * * *